United States Patent
Carabe-Fernandez

(10) Patent No.: US 10,020,161 B2
(45) Date of Patent: Jul. 10, 2018

(54) CHARGED PARTICLE SYSTEM AND METHODS FOR IRRADIATING A PLANNING TARGET VOLUME

(71) Applicant: The Trustees of the University of Pennsylvania, Philadelphia, PA (US)

(72) Inventor: Alejandro Carabe-Fernandez, Seville (ES)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 15/328,135

(22) PCT Filed: Jul. 20, 2015

(86) PCT No.: PCT/US2015/041160
§ 371 (c)(1),
(2) Date: Jan. 23, 2017

(87) PCT Pub. No.: WO2016/014422
PCT Pub. Date: Jan. 28, 2016

(65) Prior Publication Data
US 2017/0213690 A1    Jul. 27, 2017

Related U.S. Application Data

(60) Provisional application No. 62/026,832, filed on Jul. 21, 2014, provisional application No. 62/078,197, filed on Nov. 11, 2014.

(51) Int. Cl.
*A61N 5/10* (2006.01)
*A61N 5/00* (2006.01)
(Continued)

(52) U.S. Cl.
CPC ........ *H01J 37/1474* (2013.01); *A61N 5/1031* (2013.01); *A61N 5/1081* (2013.01);
(Continued)

(58) Field of Classification Search
USPC ........... 250/492.1, 492.21, 492.3, 494.1, 526
See application file for complete search history.

(56) References Cited

U.S. PATENT DOCUMENTS 7,692,168 B2    4/2010  Moriyama
8,575,564 B2 *  11/2013 Iwata ................. G21K 1/043
                                                250/396 R
(Continued)

OTHER PUBLICATIONS

International Preliminary Report on Patentability and Written Opinion for International Application No. PCT/US2015/041160, dated Jan. 24, 2017, 9 pages.
(Continued)

*Primary Examiner* — Bernard Souw
(74) *Attorney, Agent, or Firm* — RatnerPrestia

(57) ABSTRACT

A method for irradiating a planning target volume with charged particles includes delivering the charged particles to the planning target volume with a charged particle therapy system including a charged particle beam path and a gantry configured to rotate about the planning target volume and to direct the charged particle beam path; rotating the gantry, during an irradiation session, to a plurality of positions; during the rotation, irradiating the planning target volume with the charged particles at a first energy level at one or more of the plurality of positions.

21 Claims, 25 Drawing Sheets

(51) Int. Cl.
*H01J 3/14* (2006.01)
*H01J 37/147* (2006.01)
(52) U.S. Cl.
CPC ............. *A61N 2005/1087* (2013.01); *H01J 2237/1503* (2013.01); *H01J 2237/30483* (2013.01); *H01J 2237/31* (2013.01)

(56) References Cited

U.S. PATENT DOCUMENTS

| | | | |
|---|---|---|---|
| 9,084,890 B2* | 7/2015 | Iwata | G21K 1/043 |
| 9,770,604 B2* | 9/2017 | Iwata | A61N 5/1081 |
| 9,795,807 B2* | 10/2017 | Inaniwa | A61N 5/1075 |
| 2009/0296885 A1 | 12/2009 | Boeh | |
| 2010/0243911 A1* | 9/2010 | Fujii | A61N 5/1044 |
| | | | 250/400 |
| 2014/0252227 A1* | 9/2014 | Sasai | G21K 1/046 |
| | | | 250/307 |
| 2015/0041665 A1* | 2/2015 | Hollebeek | A61N 5/1071 |
| | | | 250/375 |

OTHER PUBLICATIONS

International Search Report and Written Opinion of the International Searching Authority for International Application No. PCT/2015/041160, dated Oct. 23, 2015, 10 pages.

* cited by examiner

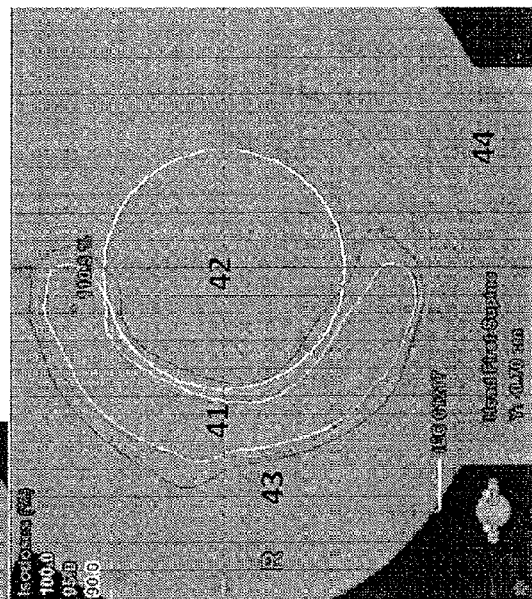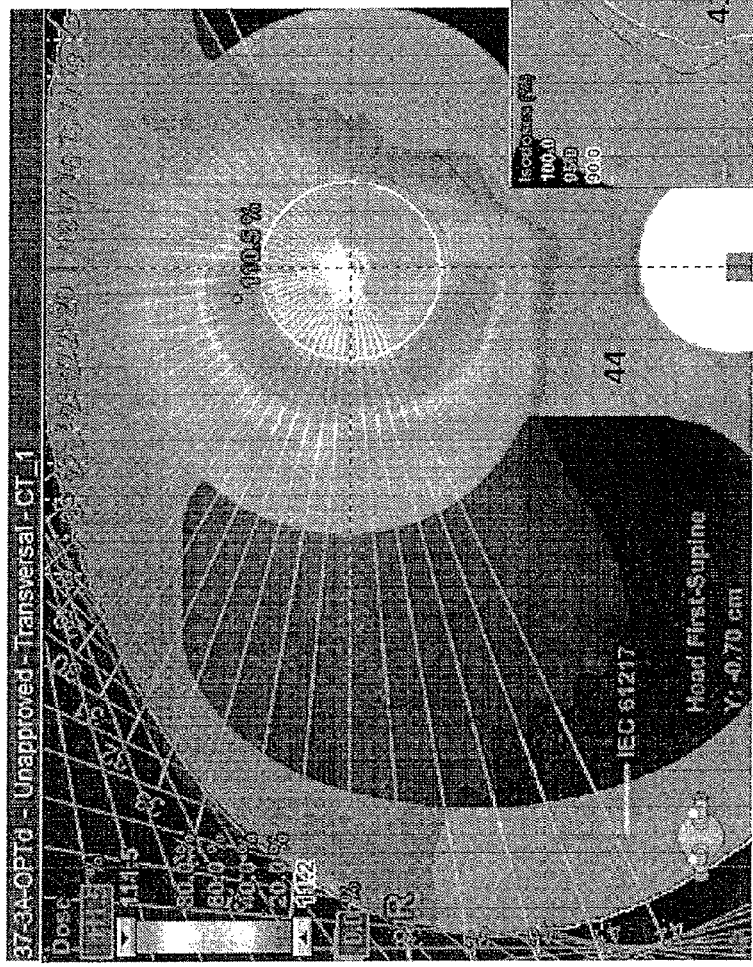
FIG. 8

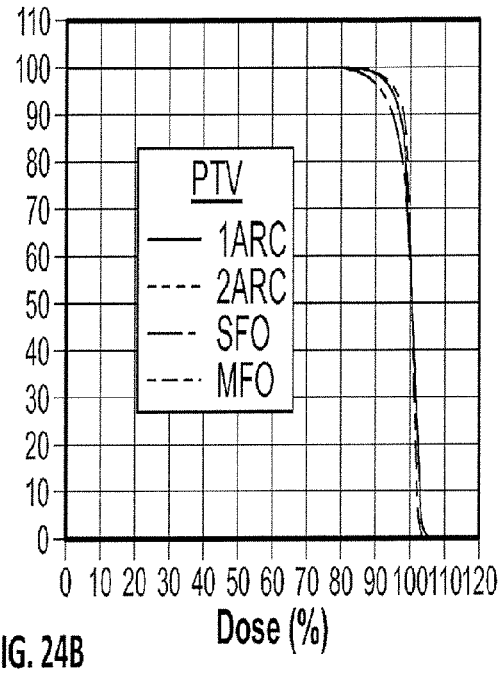
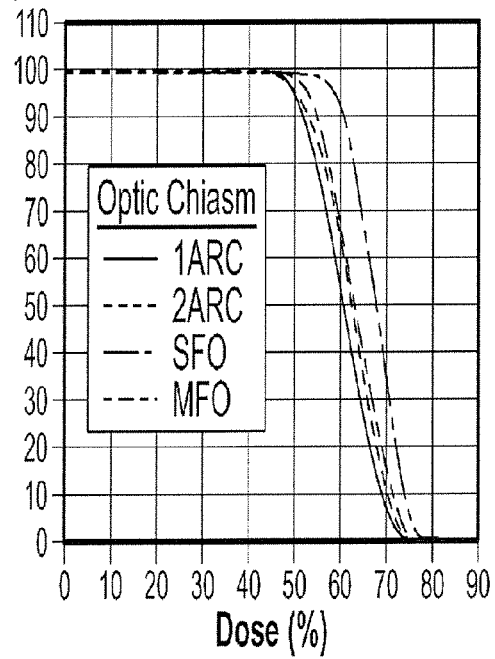
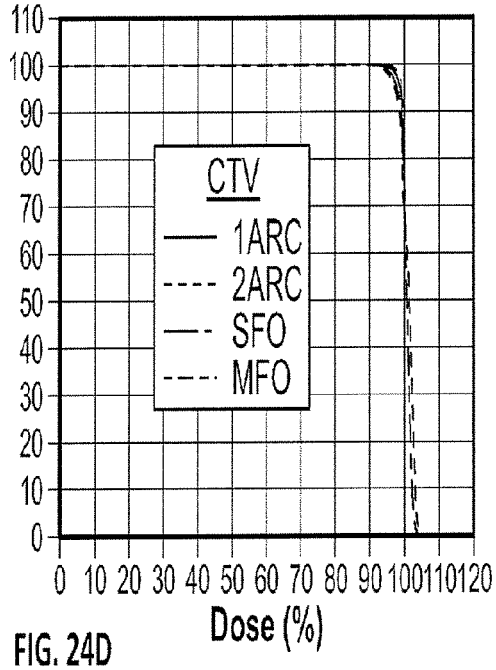
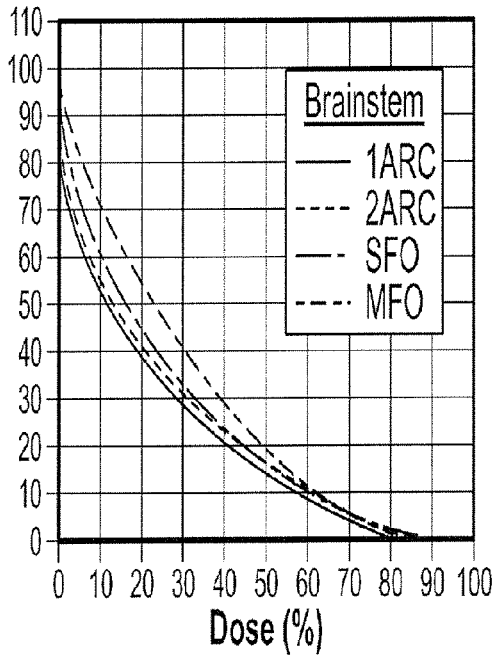

CHARGED PARTICLE SYSTEM AND METHODS FOR IRRADIATING A PLANNING TARGET VOLUME

CROSS-REFERENCE TO RELATED APPLICATIONS

This application is a National Phase Application of International Application No. PCT/US2015/041160, filed Jul. 20, 2015, entitled CHARGED PARTICLE SYSTEM AND METHODS FOR IRRADIATING A PLANNING TARGET VOLUME which claims priority to U.S. Provisional application Ser. No. 62/026,832 entitled CHARGED PARTICLE SYSTEM AND METHODS FOR IRRADIATING A PLANNING TARGET VOLUME filed on Jul. 21, 2014 and U.S. Provisional application Ser. No. 62/078,197 entitled CHARGED PARTICLE SYSTEM AND METHODS FOR IRRADIATING A PLANNING TARGET VOLUME filed on Nov. 11, 2014, the contents of which are incorporated fully herein by reference.

FIELD OF THE INVENTION

This invention relates to the field of charged particle therapy systems.

BACKGROUND OF THE INVENTION

Charged particle therapy systems have proven applications in the treatment of cancerous cells. Conventional radiation therapy uses X-rays which pass through the target volume and deliver an undesirable exit dose to healthy tissue. A charged particle beam path can be terminated at a precise location, minimizing damage to healthy tissue surrounding the target volume.

Current methods of delivering charged particles in pencil beam scanning (PBS) mode require the target volume be treated in layers, with each layer corresponding to a different charged particle beam energy level. Inter-layer switching time, which includes changing the energy level of the charged particle beam, can vary between several microseconds to several seconds and leads extended treatment times. Thus, if the dose was to be delivered while the particle gantry or patient positioning device (PPS) rotates, the radiation dose cannot be delivered fast enough to all the layers at a given gantry or PPS angle.

SUMMARY OF THE INVENTION

Aspects of the invention relate to methods for irradiating a planning target volume with charged particles, as well as charged particle therapy systems.

In one aspect of the invention, a method for irradiating a planning target volume with charged particles is provided. The method includes the steps of delivering the charged particles to the planning target volume with a charged particle therapy system including a charged particle beam path and one or more charged particle beam path direction including either or both of a gantry configured to rotate about the planning target volume and a patient positioning device configured to rotate the planning target volume; rotating the charged particle beam path direction devices, during an irradiation session, to a plurality of positions, and during the rotation, irradiating the planning target volume with the charged particles at a first energy level at one or more of the plurality of positions. At each of the one or more plurality of positions, the charged particle beam path terminates within the planning target volume to produce a Bragg peak within the planning target volume.

In another aspect of the invention, a method for irradiating a planning target volume with charged particles is provided. The method includes the steps of delivering the charged particles to the planning target volume with a charged particle therapy system including a charged particle beam path and one or more charged particle beam path direction devices including either or both of a gantry configured to rotate about the planning target volume and a patient positioning device configured to rotate the planning target volume, which directs the charged particle beam path; rotating the one or more charged particle beam path direction devices, during an irradiation session, to a plurality of positions, and during the rotation, irradiating the planning target volume with the charged particles at a first energy level at one or more of the plurality of positions.

In yet another aspect of the invention, a charged particle therapy system is provided. The system includes a charged particle beam path and one or more charged particle beam path direction devices including either or both of a gantry configured to rotate about a planning target volume and to deliver charged particles while rotating and a patient positioning device configured to rotate the planning target volume such that the charged particle beam path terminates within the planning target volume to produce a Bragg peak within the planning target volume.

It is to be understood that both the foregoing general description and the following detailed description are exemplary, but are not restrictive, of the invention.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. This emphasizes that according to common practice, the various features of the drawings are not drawn to scale unless otherwise indicated. On the contrary, the dimensions of the various features may be expanded or reduced for clarity. Included in the drawings are the following figures:

FIG. 8 is an image of an elliptical non-uniform phantom containing a defined non-symmetrical planning target volume that has been irradiated with charged particles according to aspects of the present invention;

FIGS. 24A-24D are images comparing the dosage delivered to healthy tissue under standard treatment plans to treatment plans in accordance with aspects of the present invention.

DETAILED DESCRIPTION OF THE INVENTION

Aspects of the invention are directed to methods for irradiating a planning target volume with charged particles and charged particle therapy systems. The following descriptions are meant to provide example embodiments of the present invention. The scope of the claims is not intended to be limited by any of the particular embodiments disclosed below.

The inventor has recognized that it would be useful to provide a charged particle therapy treatment method that combines pencil beam scanning and arc therapy techniques. The inventor has additionally recognized that utilizing a single energy for each arc or segment of an arc about the planning target volume reduces exposure time and the number of monitor units required for the treatment process. In particular, the inventor has found that with only one energy per angle, the speed of the treatment becomes limited only by the rotational speed of the gantry and the length of the arc(s) used for the treatment. The inventor has further recognized that terminating the Bragg peak in the central region of the planning target volume minimizes the dose of radiation to the surrounding healthy tissue and increases linear energy transfer (LET) of the charged particle beam in the target.

Figure 1:
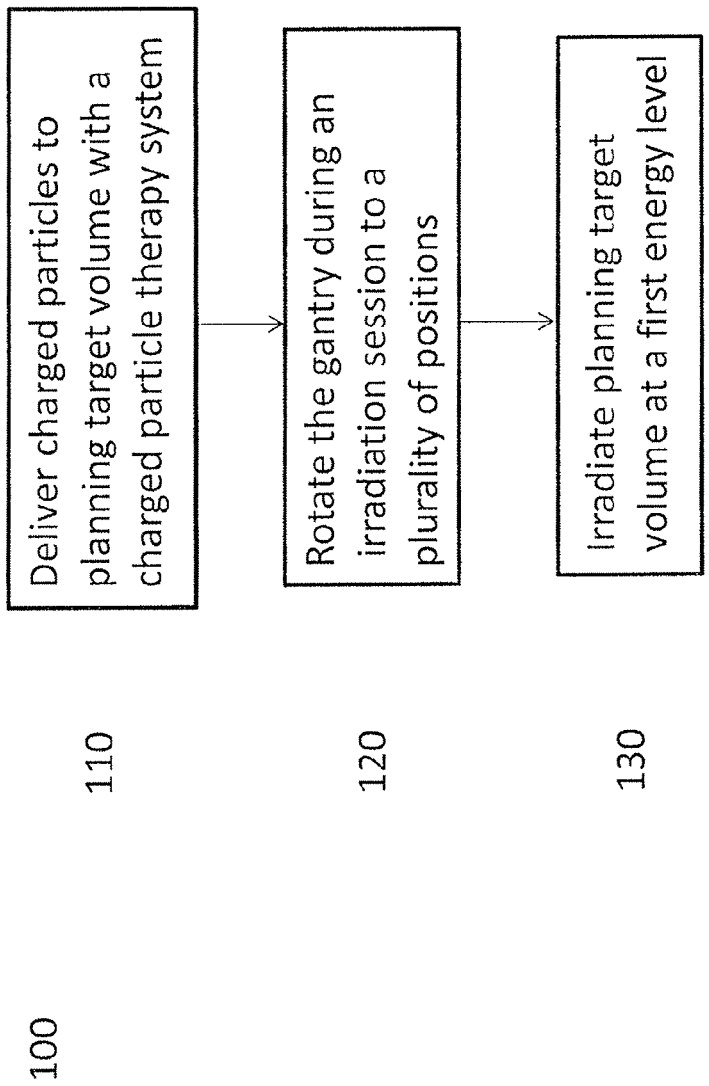
FIG. 1 is a block diagram of a method for irradiating a planning target volume with charged particles according to aspects of the present invention.

FIG. 1 shows in schematic form a method 100 for irradiating a planning target volume with charged particles. The method may be performed using a charged particle therapy system including a charged particle beam path and a gantry configured to rotate about a planning target volume. Additionally or alternatively, the charged particle therapy system may include a charged particle beam path and a patient positioning device ("PPS") configured to rotate the planning target volume, e.g., by rotating the patient. One of ordinary skill in the art will understand upon reading this disclosure that other suitable devices and/or pieces of equipment may be utilized to manipulate the charged particle beam with reference to the planned target volume.

In one embodiment, the charged particle therapy system operates in pencil beam scanning (PBS) mode. In step 110, the charged particle therapy system delivers charged particles to a planning target volume. The planning target volume is a geometrical concept defined to deliver radiation. The planning target volume may be a uniform or non-uniform phantom for use in treatment planning, or a tumor in a patient. One of ordinary skill in the art will understand that the size and shape of the planning target volume depend on the size of the area to be treated (e.g., the tumor volume) treatment technique used, the effects of organ and patient movement, and inaccuracies in beam and patient setup.

In step 120, a gantry is rotated during an irradiation session (e.g., during the delivery of radiation to a planning target volume of a patient) to a plurality of positions in an arc about the planning target volume. An arc includes at least a portion of 360 degrees about the planning target volume. An irradiation session may include multiple arcs, where each arc may have the same or different center of rotation and where each arc may be contained in the same plane of rotation (co-planar arcs) or not contained in the same plane of rotation (non-coplanar arcs). The gantry transports and delivers the charged particle beam into a treatment room, bends the beam until it can be incident orthogonal to the patient and then rotates the beam around the patient. A typical gantry is comprised of large magnets, an evacuated pipe, a nozzle and a counterweight. All of the components are mounted on a large steel beam "squirrel cage" to enable the rotation of the proton beam around the patient. In a preferred embodiment, the gantry is operable to continuously rotate while simultaneously delivering charged particles to the planning target volume, which decreases treatment time and increases efficiency. The gantry may rotate continuously and deliver charged particles to a plurality of positions within the arc. The rotation may be centered on the planning target volume, or it may be centered elsewhere. In one embodiment, the gantry rotates continuously, but delivers charged particles to less than all positions within the arc, i.e., it does not deliver charged particles to the entire arc.

In an alternative embodiment, a PPS may be used to rotate the patient to a plurality of positions with respect to a fixed charged particle beam. The PPS may rotate continuously during the treatment of the patient, thereby decreasing treatment time and increasing efficiency.

In step 130, the planning target volume is irradiated at a first energy level. Irregularly shaped planning target volumes, such as the elliptical, non-uniform phantom depicted in FIG. 6, may require multiple charged particle beam energy levels to deliver a dose to the entire target. In one embodiment, prior to the delivering the dose to the target volume, the planning target volume is subdivided into a plurality of sub-targets, which may form a plurality of positions towards which the charged particle beams are directed.

The charged particle beam path may terminate within the target volume such the Bragg peak is located within the planning target volume. Preferably, the particle beam path terminates within the target volume such the Bragg peak is located in a central region of the planning target volume The Bragg peak is a pronounced peak on the Bragg curve which plots the energy loss of ionizing radiation during its travel through matter. Protons in particular tend to travel through the body tissue without significant absorption until they reach a specific point within the body. At this point, which corresponds to the Bragg peak of the proton beam, the proton energy is released. For protons, the peak occurs immediately before the particles come to rest. Thus, the region where the Bragg peak is located receives the highest dose from the charged particle beam. Tracking the central region of the planning target volume with the proton beam Bragg peak minimizes damage to surrounding healthy tissue such as, e.g., organs at risk ("OARs") and maximizes the dose and linear energy transfer (LET) received by the planning target volume from the charged particle beam.

Figure 2:
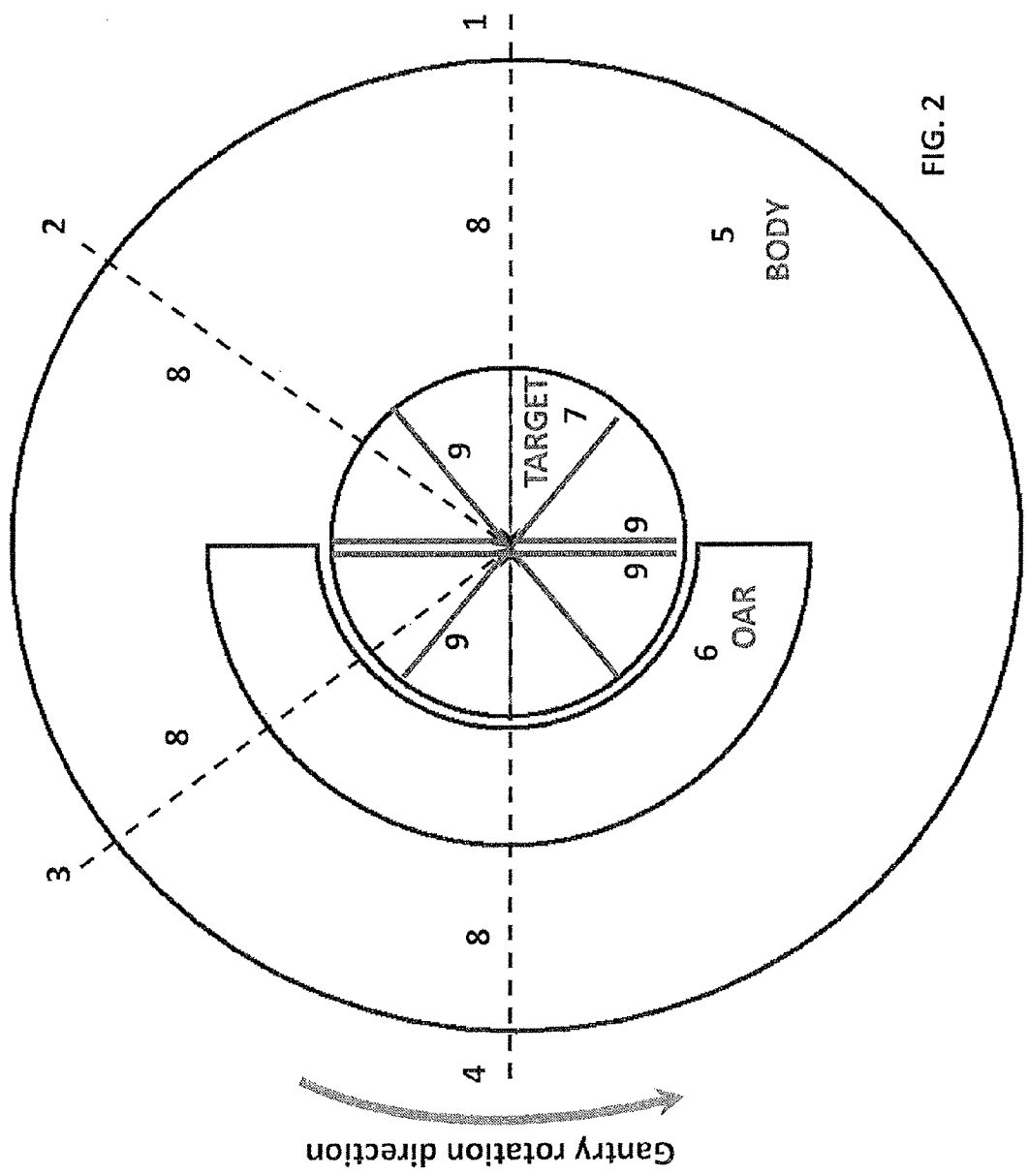
FIG. 2 is a schematic illustration of an irradiation session involving irradiating a symmetrical planning target volume with charged particles according to aspects of the present invention.

FIG. 2 depicts a schematic diagram of the irradiation of a planning target volume according to aspects of the present invention. A circular uniform phantom represents a patient body 5 with an OAR 6 surrounding a circular uniform planning target volume 7. The gantry (not shown) rotates continuously from position 1 to position 4 about the planning target volume 7. In this embodiment, the gantry rotates a half arc about the planning target volume. The charged particle beam 8, at a first energy level, enters the patient body 5 and terminates such that the Bragg peak is located in the central planar region of the planning target volume 7. The charged particle beam 8 may be directed to one or more of the plurality of positions between position 1 and position 4, i.e., positions 2 and 3, or other positions not depicted. Also, the charged particle beam path may be shut off at one or more of the plurality of positions. While the charged particle beam path is shut off, the gantry does not irradiate the planning target volume, however, as described above, the gantry may continue to rotate.

Figure 3:
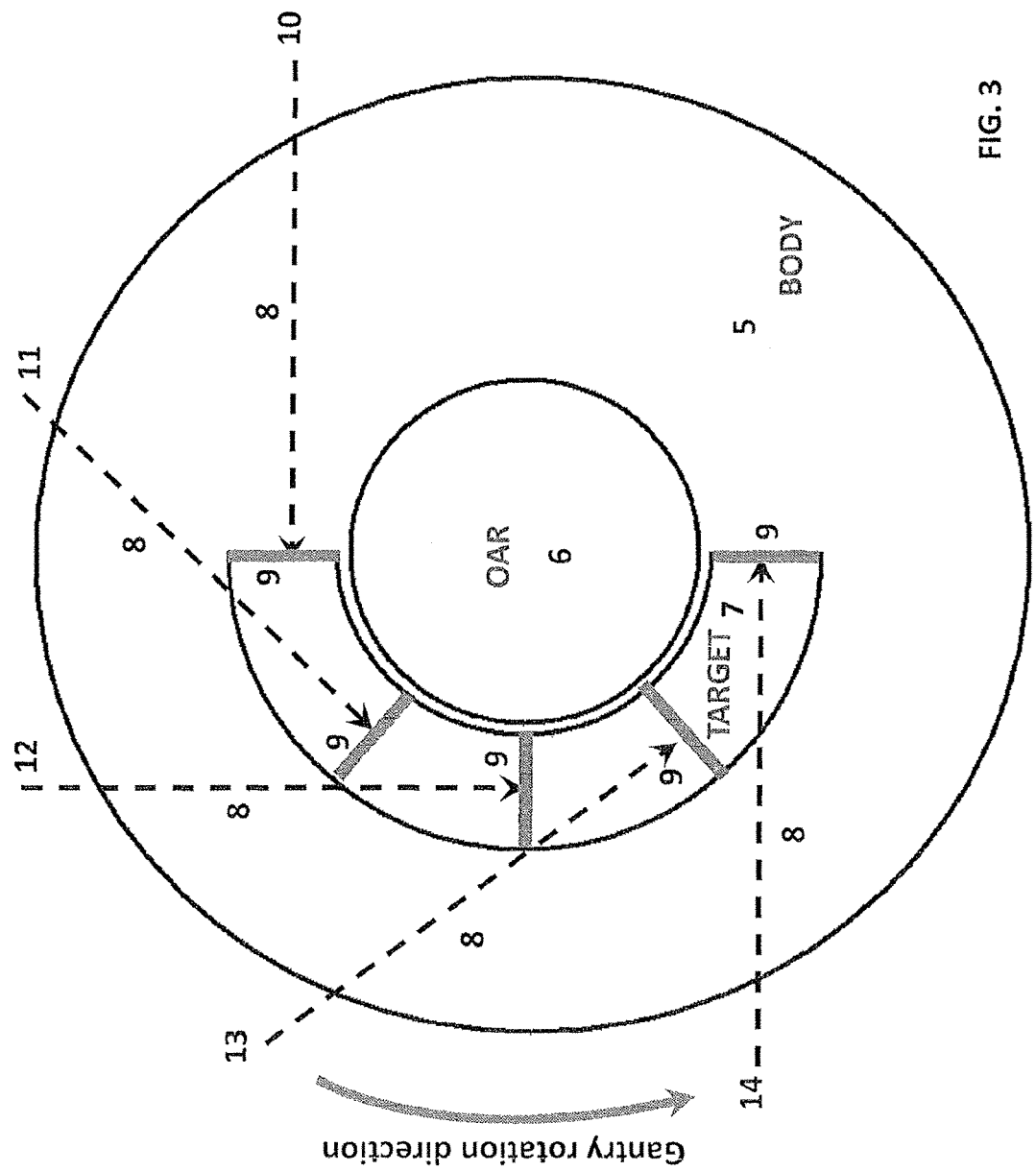
FIG. 3 is a schematic illustration of an irradiation session involving irradiating a non-symmetrical planning target volume with charged particles according to aspects of the present invention.

As shown in FIG. 3, irradiation may be applied to a more complex planning target volume geometry. A uniform circular phantom represents a patient body 5 with nonsymmetrical target 7 surrounding an OAR 6. In this embodiment, the gantry is configured to rotate isocentrically approximately 180 degrees (i.e., a half arc) about the planning target volume to a plurality of positions. The plurality of positions may be located at various points within the 180 degrees about the planning target volume, as demonstrated by example positions 10, 11, 12, and 13. The gantry delivers beams 8 at a first energy level while rotating between positions 10 and 14. The gantry may rotate from position 10 to position 14, or from position 14 to position 10. Bragg peaks 9 deposit energy in the section of the plane perpendicular to beams 8 that contains the target.

Figure 4:
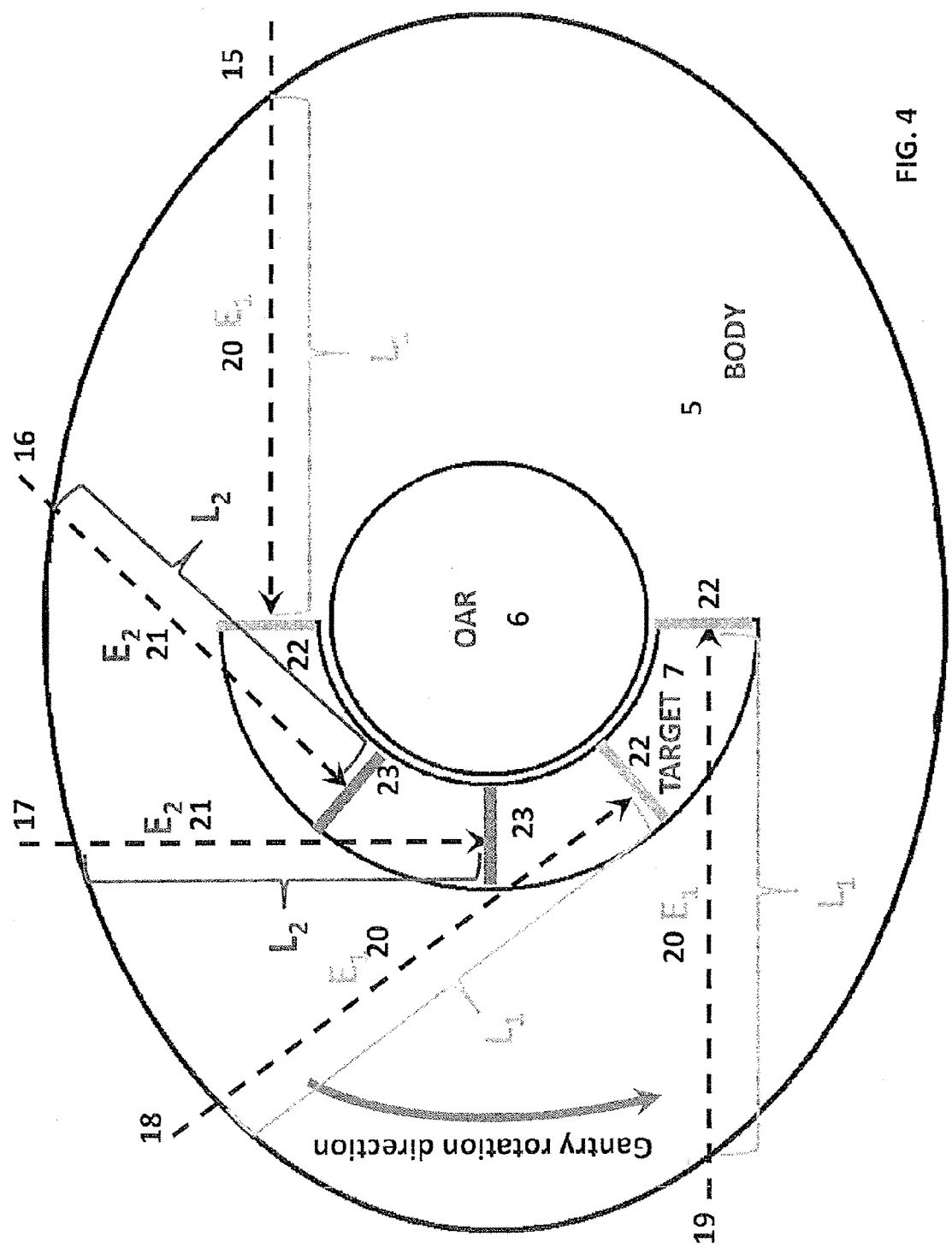
FIG. 4 is a schematic illustration of an irradiation session involving irradiating a non-symmetrical planning target volume with charged particles according to aspects of the present invention.

Turning to FIG. 4 an elliptical phantom represents a patient body 5 with nonsymmetrical target 7 surrounding OAR 6. In this embodiment, the gantry is configured to complete two 180 degree (i.e., two half arc) rotations and deliver charged particles at a first and second energy level. Each rotation may correspond to a distinct energy level. As the gantry rotates about target 7 to irradiate planes 22 (corresponding to a first energy level $E_1$) and 23 (corresponding to a second energy level $E_2$), the depth ($L_1$, $L_2$, . . . ) of each of these planes may vary for each individual gantry angle requiring the use of more than one energy ($E_1$, $E_2$, . . . ) to deposit the dose in the PTV. While only five planes 22 and 23 are shown, irradiation may be continuous. In this embodiment, two beam energies are used due to the non-symmetrical shape of the patient body 5. Different energies may be required to penetrate to the required depth at every angle so that the Bragg peak terminates in the target volume.

While rotating from position 15 to position 16, the gantry delivers a charged particle beam 20 to a plane contained within the planning target volume 7. The charged particle beam is shut off when the gantry reaches position 16. The gantry continues to rotate and, when it reaches position 18, the charged particle beam is turned back on at the first energy level. The charged particle beam irradiates the planning target volume at the first energy level until the gantry reaches position 19. At this position, the charged particle beam is shut off, and the gantry stops, completing its first of two rotations.

The charged particle beam is then configured to emit charged particles at a second energy level which is distinct from the first. The gantry then rotates back from position 19 to position 15. When the gantry reaches position 17, the charged particle beam 21 irradiates the planning target volume 7 at a second energy level as the gantry continues to rotate. When the gantry reaches position 16, the charged particle beam is shut off and the gantry continues to rotate until it reaches position 15, completing its second rotation.

Figure 5:
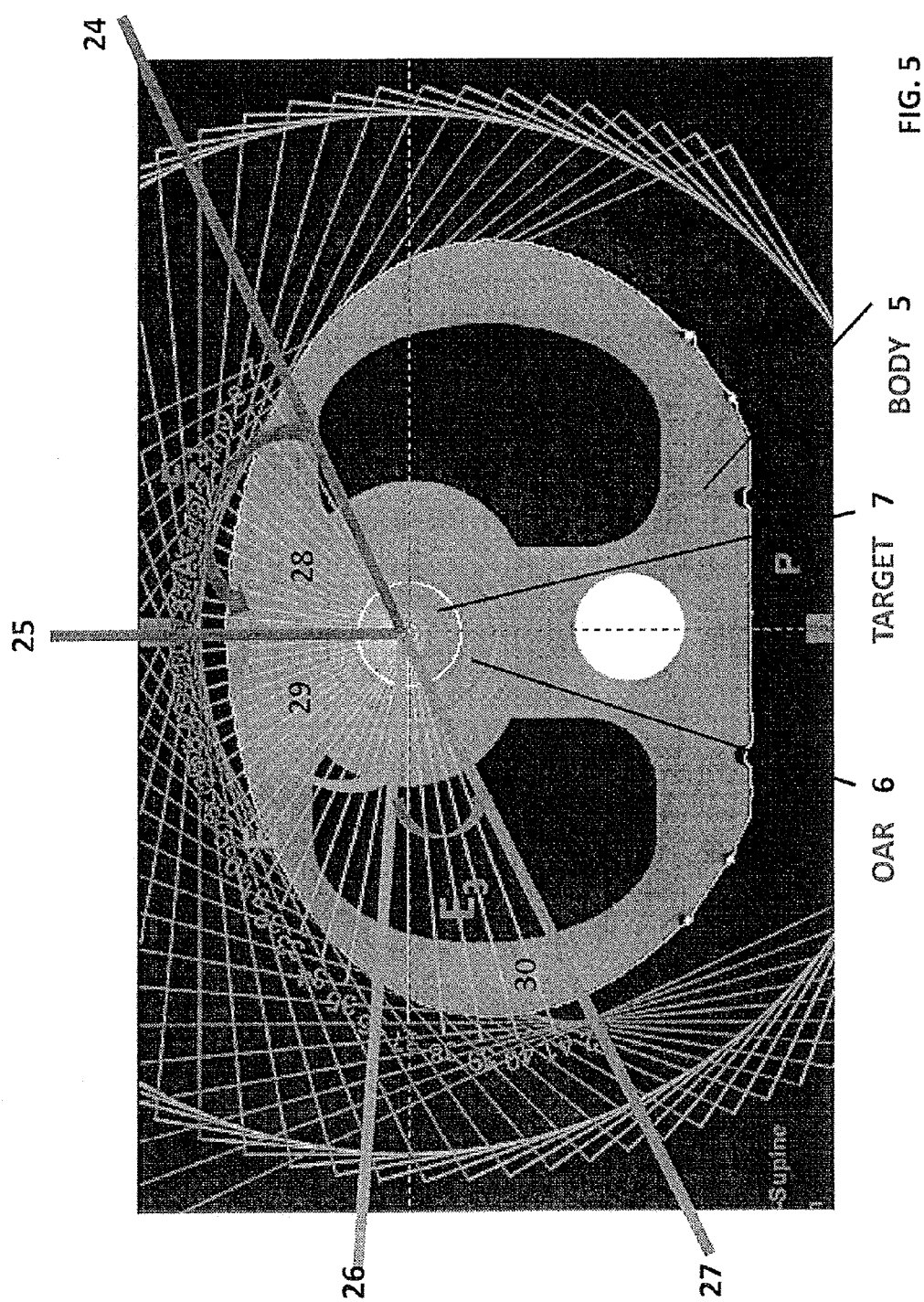
FIG. 5 is a schematic illustration of an irradiation session involving irradiating an irregular phantom with a non-symmetrical planning target volume with charged particles according to aspects of the present invention.

FIG. 5 illustrates the irradiation of a planning target volume according to principles of the present invention. In this embodiment, three distinct energy levels are used, corresponding with three gantry rotations, due to the non-symmetrical nature of the planning target volume and patient body. In this example, the gantry rotates counter-clockwise with respect to the planning target volume in a continuous arc starting at position 24 and ending at position 27. Between position 24 and position 25, the gantry delivers a charged particle beam 28 at a first energy level $E_1$ to the planning target volume 7. During this first rotation and during the two subsequent rotations, the charged particle beam path terminates such that Bragg peak is located within the planning target volume 7 in a similar fashion to FIG. 4. Once it reaches position 25, the gantry shuts off the charged particle beam while continuing its rotation about the planning target volume to position 27. The gantry then begins its second rotation, rotating clockwise with respect to the planning target volume from position 27 to position 25. Between position 26 and position 25, the gantry delivers a charged particle beam 29 at a second energy level $E_2$. The gantry then shuts off the charged particle beam and stops. The gantry then completes a third rotation, rotating counterclockwise with respect to the planning target volume 7 from position 25 to position 27. Between position 25 and position 26 the gantry rotates without delivering any dose and once it reaches position 26, the charged particle beam 30 is turned back on at a third energy level $E_3$. The gantry rotation and charged particle beam both stop when the gantry reaches position 27 during its third rotation.

One of ordinary skill in the art will understand that the gantry may rotate more than three times, and that more than three energy levels may be used in an irradiation session while still remaining within the scope of the present invention.

EXAMPLES

Figure 6:
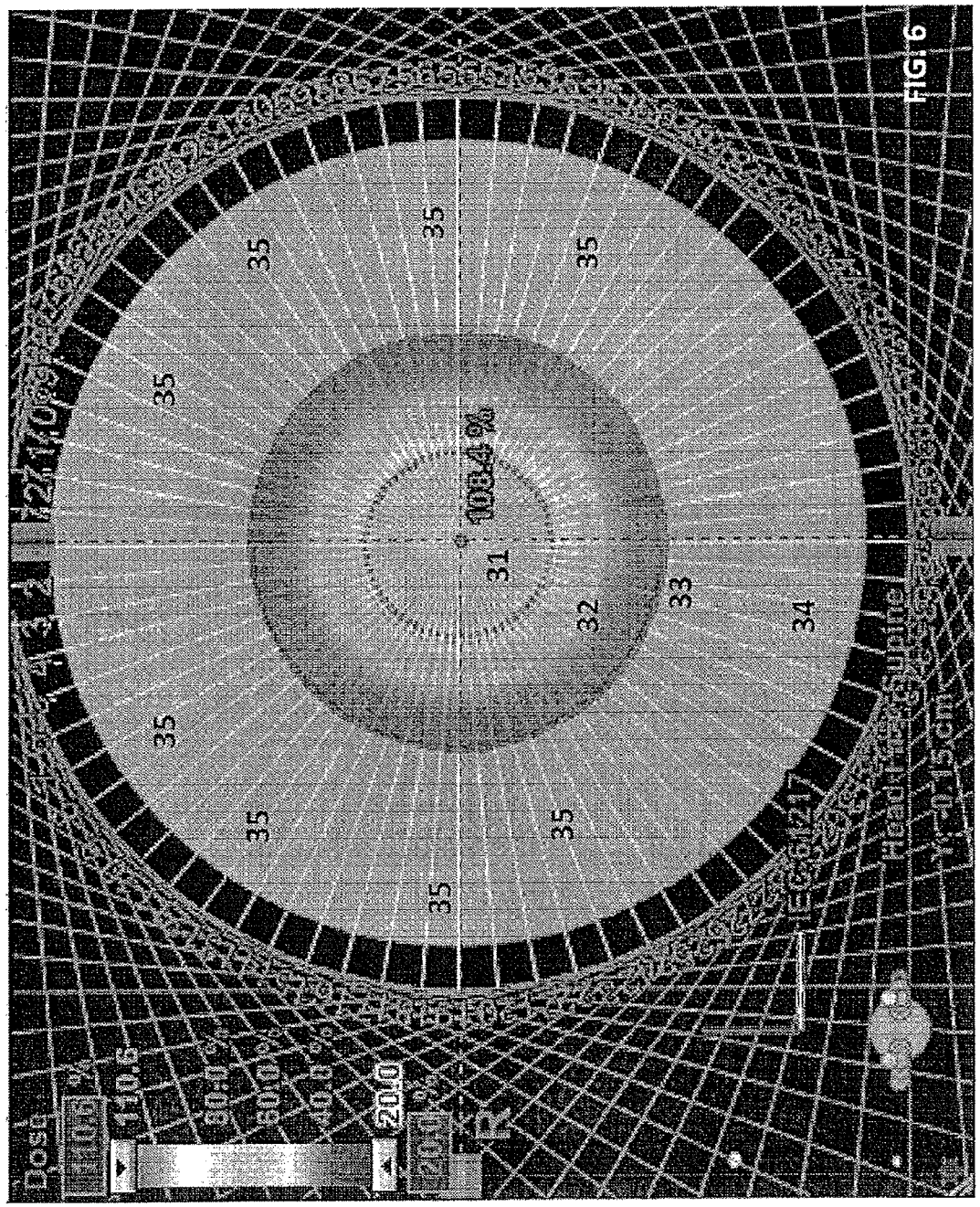
FIG. 6 is an image of a circular uniform phantom containing a defined symmetrical planning target volume that has been irradiated with charged particles according to aspects of the present invention.

Example 1—Proton Modulated Arc Therapy in a Circular Uniform Phantom with a Symmetrical Planning Target Volume The delivery of a uniform dose to a planning target volume using pencil beam scanning proton modulated arc therapy was performed. FIG. 6 shows the dose distribution in the central plane of a cylindrical phantom, and depicts the charged particle dose distribution (dose in color wash) obtained when beams are delivered as described in FIG. 2. A planning target volume 31 and OARs 32 and 33 were defined within a cylindrical, homogeneous phantom 34. Planning target volume 31 is a circle 5 cm in diameter. A 166.94 MeV proton beam 35 was used in a 360 degree arc, the beam entering the planning target volume at a plurality of positions. The radiation dose was concentrated in planning target volume 31. As shown by the dose density diagram, dose delivery to OAR's 32 and 33 was minimal.

Figure 7:
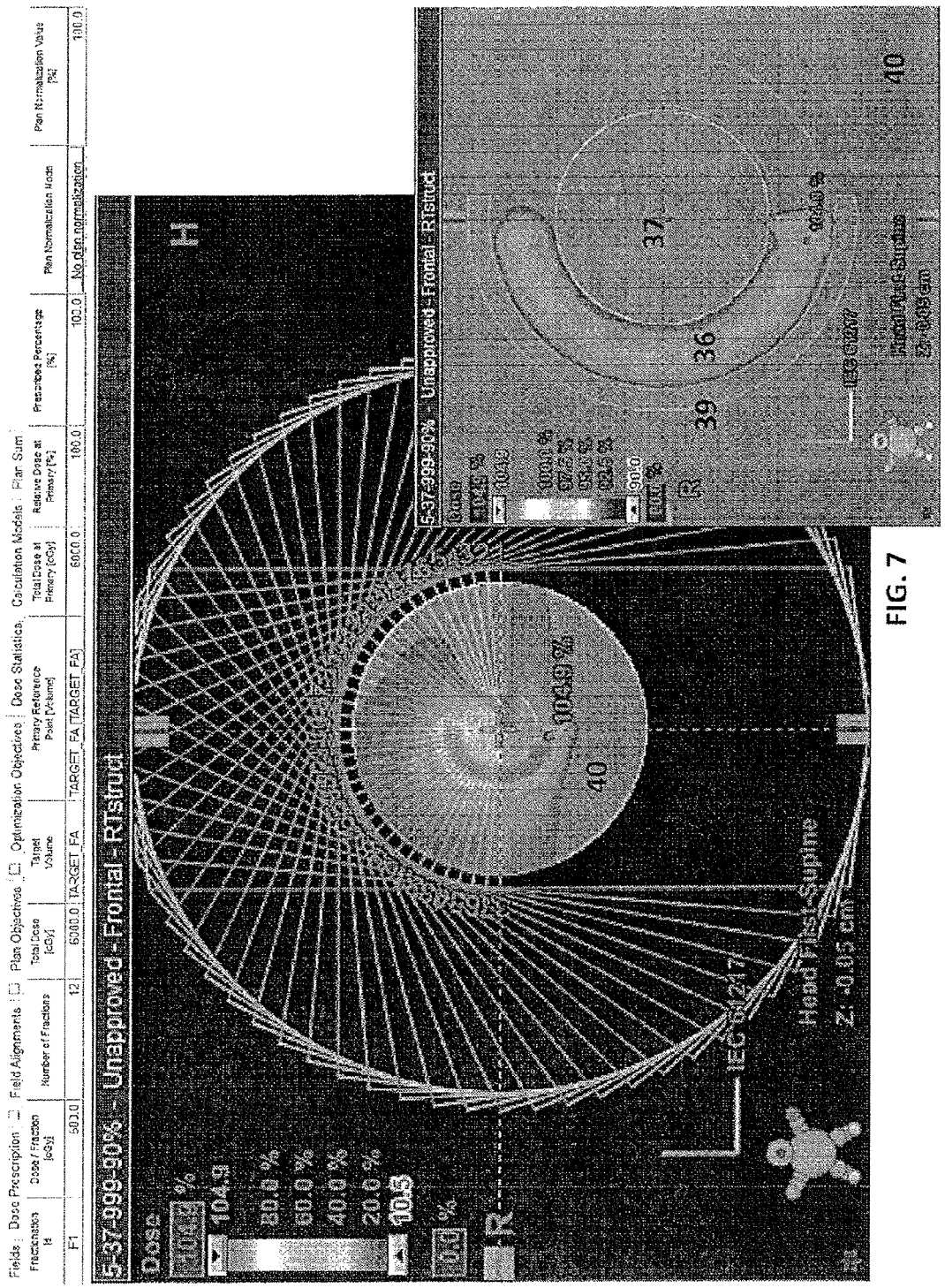
FIG. 7 is an image of a circular uniform phantom containing a defined non-symmetrical planning target volume that has been irradiated with charged particles according to aspects of the present invention.

Example 2—Proton Modulated Arc Therapy in a Circular Uniform Phantom with a Non-Symmetrical Planning Target Volume The delivery of a uniform dose to a non-symmetrical planning target volume using pencil beam scanning proton modulated arc therapy was performed. FIG. 7 shows the dose distribution in the central plane of a cylindrical phantom, and depicts the charged particle dose distribution obtained when beams are delivered as described in FIG. 3. A planning target volume 36 and OARs 37 and 39 were defined within a cylindrical, homogeneous phantom 40. Planning target volume 36 is a 1.25 cm wide half-annulus that has the same center point as OAR 37. OAR 37 is a cylinder 5 cm in diameter. There is a 2 mm separation between OAR 37 and planning target volume 36. OAR 39 is a half-annulus 0.5 cm wide and is separated by 1.5 mm from the planning target volume. Once the optimal beam energy was selected, the same beam was repeated in 37 gantry positions every 5 degrees to create a 180 degree arc. Dose delivery to the OAR was minimal.

Example 3a—Proton Modulated Arc Therapy in an Elliptical Non-Uniform Phantom

Proton modulated arc therapy was applied to irregular, nonhomogeneous shapes as may be found in the human body. FIG. 8 shows the dose distribution in the central plane of a non-uniform phantom meant to emulate a human torso, and depicts the charged particle dose distribution obtained when beams are delivered as described in FIG. 4. Planning target volume 41 and OARs 42 and 43, which have the same dimensions as in the previous example, were defined in a nonhomogeneous phantom 44. The dose distribution was obtained after using 3 different energies, as depicted in FIG. 5. The results shown in FIG. 8 indicate this treatment method could successfully be used in treatment sites with large heterogeneities such as the brain, neck, and prostate.

Example 3b—Proton Modulated Arc Therapy in an Elliptical Non-Uniform Phantom

Figure 11:
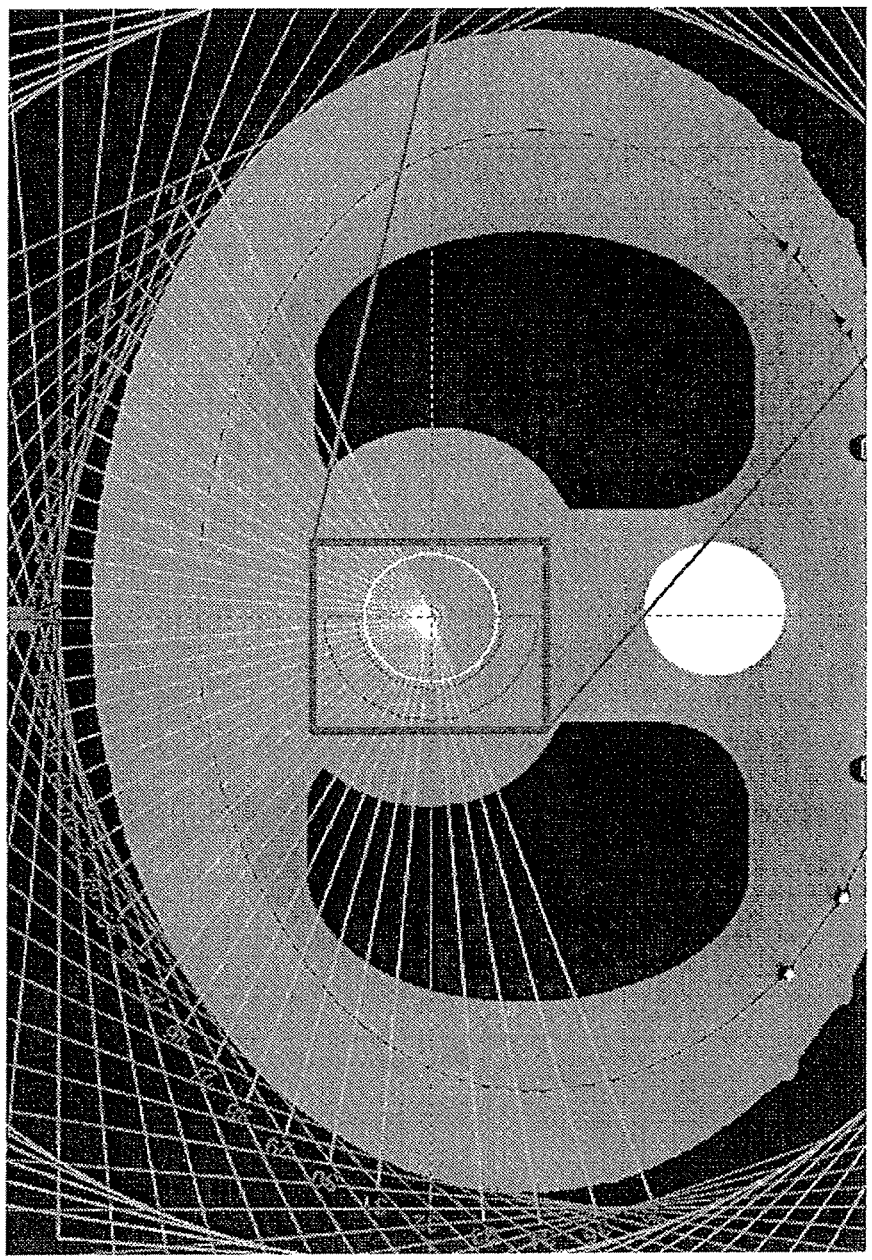
FIG. 11 is an image of an elliptical non-uniform phantom containing a defined annular target that has been irradiated with charged particles according to aspects of the present invention.

The delivery of a uniform dose to a non-symmetrical planning target volume using pencil beam scanning proton modulated arc therapy was performed. The phantom modeled phantom extended 20 cm caudad/cephalad. The target was a half annulus 1 cm wide that has the same center as the central cylinder and surrounds it by 180°. There is a 3 mm separation between the central cylinder and the half annulus. Therefore, the annulus has an inner radius of 2.3 cm and an outer radius of 3.3 cm with respect to the common central axis of the cylinder and the annulus. The structures extend 4 cm caudad/cephalad. The results shown in FIG. 11 indicate that this treatment method could be successfully used in treatment sites of non-regular shaped body parts with non-homogeneous media.

Example 4a—Proton Modulated Arc Therapy in Real Patient Geometry

Figure 9:
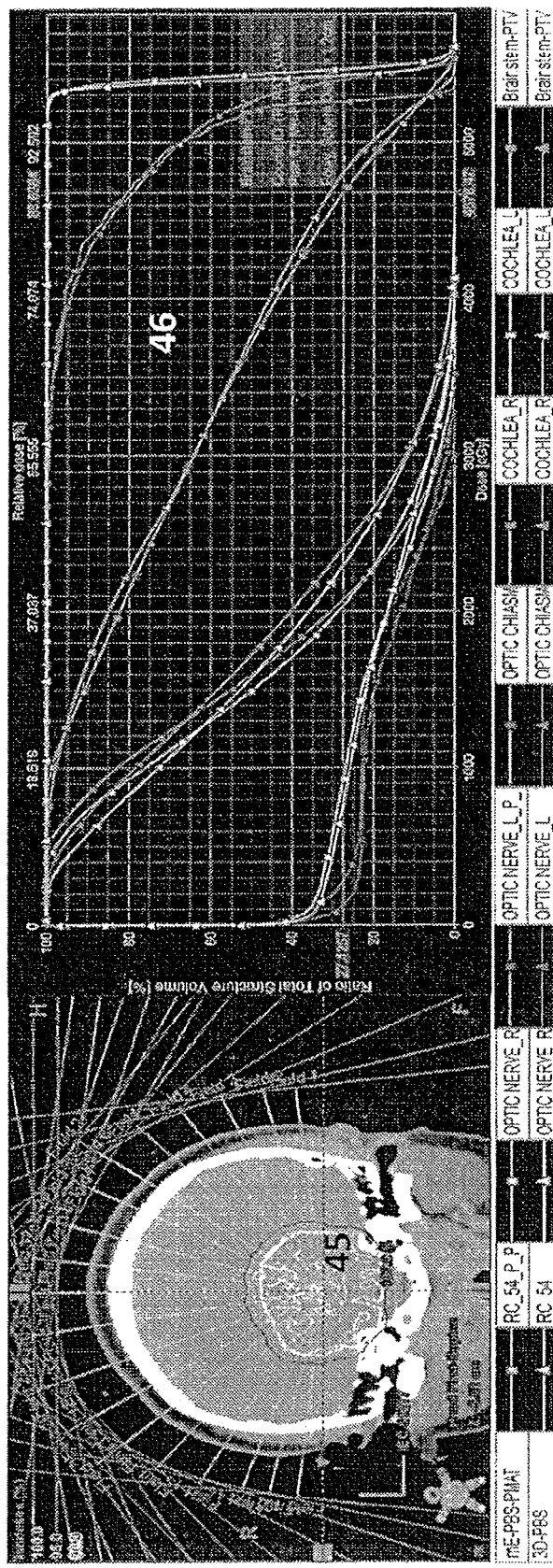
FIG. 9 is an image of a brain astrocytoma that has been simulated for the delivery of charged particles according to aspects of the present invention.
Figure 25A:
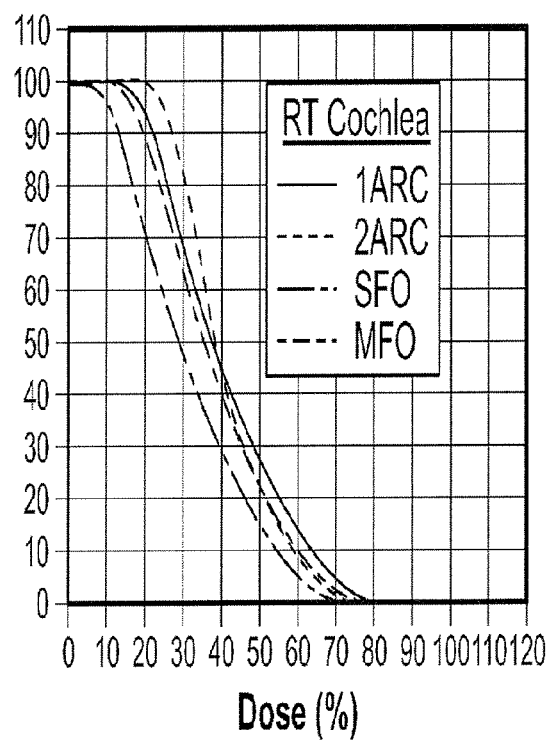
FIGS. 25A-25B are images comparing the dosage delivered to healthy tissue under standard treatment plans to treatment plans in accordance with aspects of the present invention.
Figure 25B:
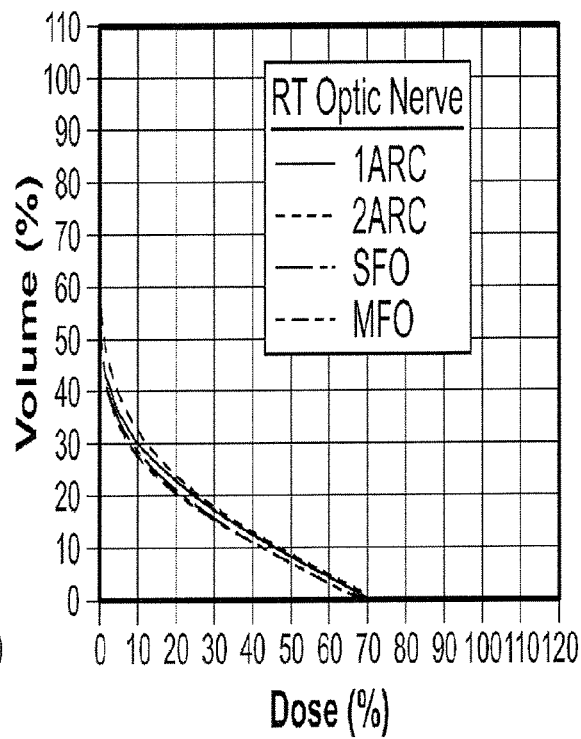

Proton modulated arc therapy was used to plan the treatment of an astrocytoma in the brain, as shown in FIG. 9. Planning target volume 45 was irradiated from a plurality of angles using a 180 degree gantry arc. The target is located in a non-homogenous location (i.e., the base of the skull) and the beam traverses the cranial bone which has a different thickness for each of the beam angles. Dose volume histogram 46 shows better sparing of healthy tissue achieved using proton modulated arc therapy (square plot symbols) when compared with results from a standard pencil beam scanning method (triangle plot symbols). FIGS. 24 and 25 further illustrates that the proton modulated arc therapy better spares healthy tissue when compared to standard methods for irradiating a patient.

Example 4b—Efficiency Assessment for Proton Modulated Arc Therapy in Real Patient Geometry An efficiency assessment of a brain case was planned using aspects of the invention as set forth above. The arcs were coplanar within an axial plane containing the isocenter and extended for 180° with 37 fields separated every 5°. The prescription used for the target and OARs is given in table 1. The beam ranges utilized for one (1E), two (2E), and three (3E) mono-energetic arcs are plotted in FIGS. 12, 13, and 14, respectively.

TABLE 1 dose prescription for the brain case presented

| Volume Name | $D_{max}$ (%) | Volume (%) | Prescribed dose (%) |
|---|---|---|---|
| CTV |  | 99 | 98 |
| PTV | 107 | 98 | 95 |
| Brainstem | 84.6 | 50 | 68.2 |
| Optic nerves & chiasm | 78.3 |  |  |
| Cochlea | 37.9 |  |  |
| Eyes | 12.6 |  |  |
| Temp lobes | 25.3* |  |  |
| Pituitary | 56.8 |  |  |
| Hippocampus | 25.3 |  |  |
| Hypothalamus | 12.6 |  |  |

*Mean Dose

In the case of the 3 mono-energetic arcs for the uniform phantom case (FIG. 14), the beam ON sequence would start delivering the arc with 14.39 cm beam range when the gantry rotates anticlockwise from angle 90° to 65°, then turn the beam OFF from angle 65° to 290°, then turn the beam back ON from 290° to the end of the first rotation (270°). At this point, the beam energy would be reduced in order to deliver a beam with a range of 12.65 cm, which will be delivered between the arc segments going from 295° to 310° and 45° to 60°, while the gantry is rotated clockwise up to gantry angle 60° where the beam is turned OFF and the gantry stops. Finally, the gantry rotates back anticlockwise to gantry angle 45° where a beam with a range of 10.91 cm is turned back ON while the gantry keeps rotating up to 315°. At this gantry angle, the beam is turned OFF and the gantry stops; thus, concluding the treatment.

Figure 12:
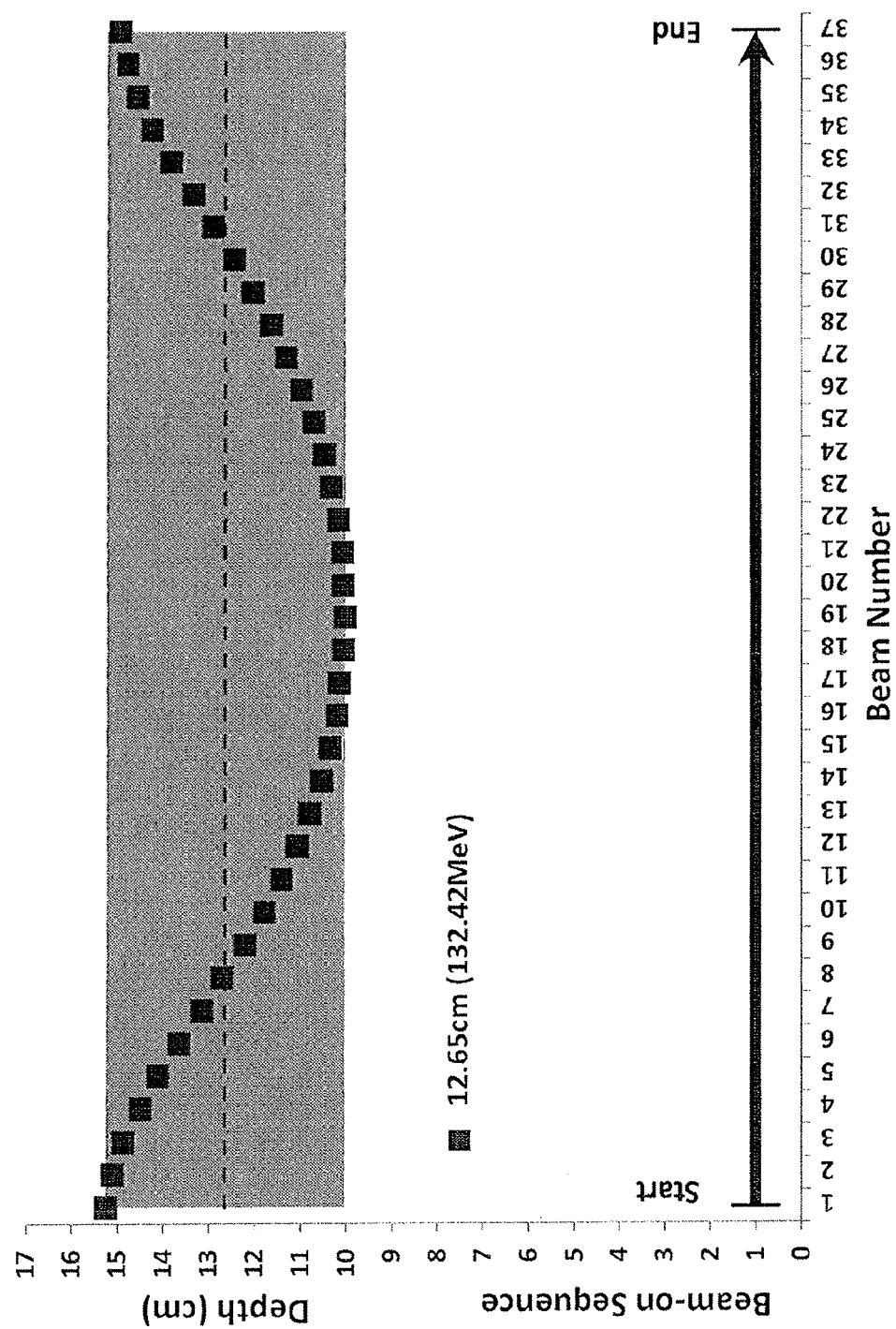
FIG. 12 is a schematic of the beam range for treatment of a real patient's brain with one mono-energetic arc according to aspects of the present invention.
Figure 13:
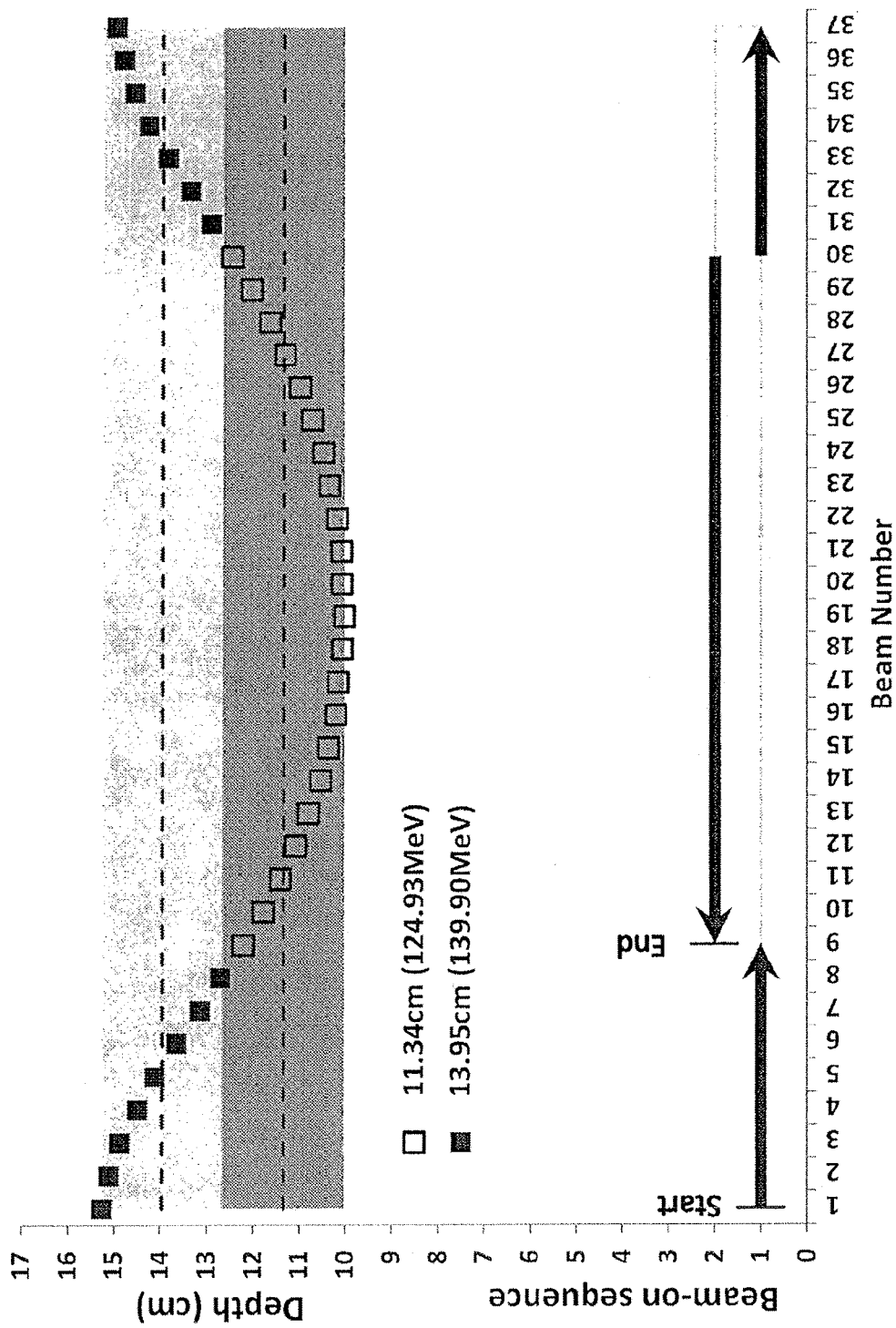
FIG. 13 is a schematic of the beam ranges for treatment of a real patient's brain with two mono-energetic arcs according to aspects of the present invention.
Figure 14:
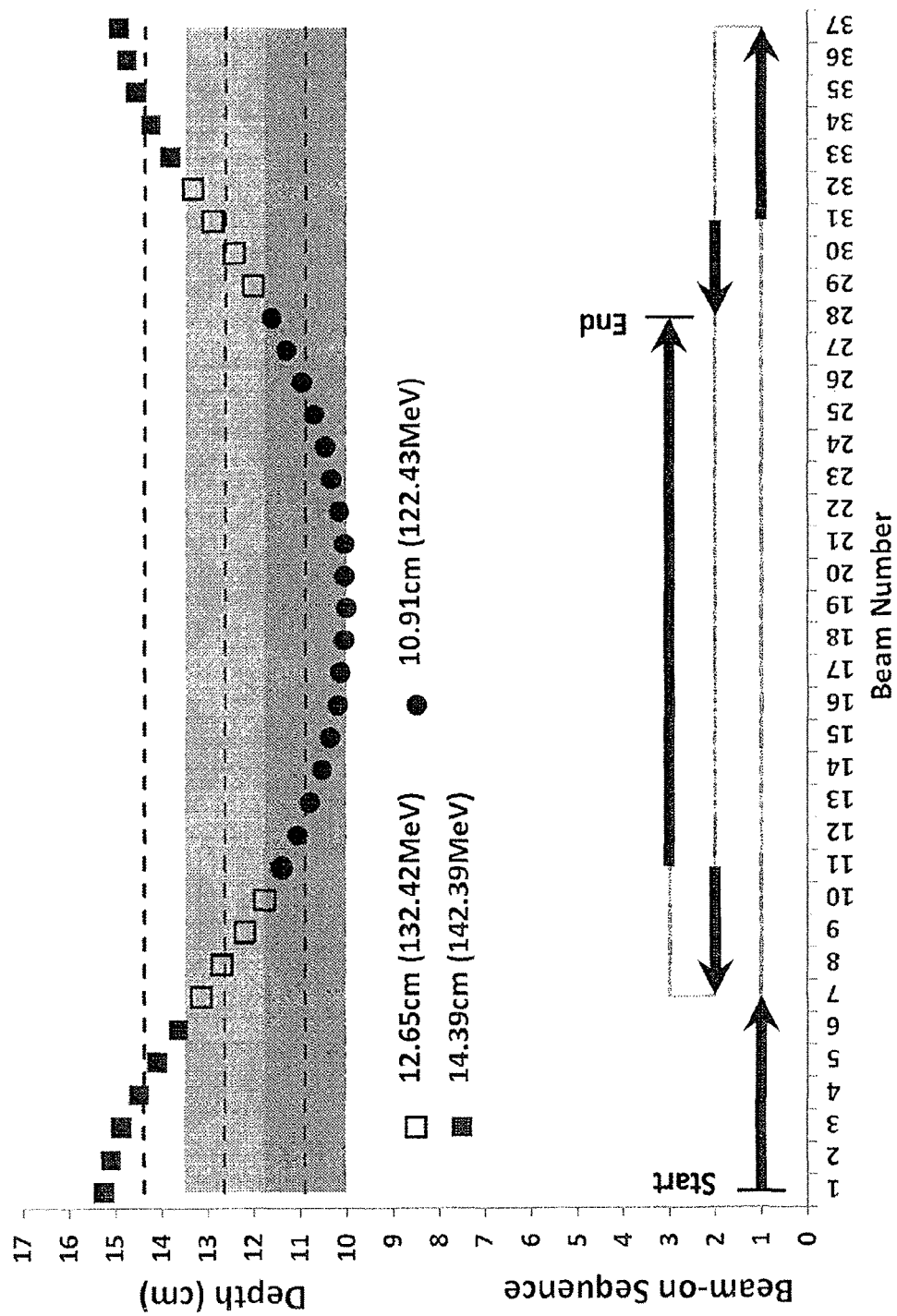
FIG. 14 is a schematic of the beam ranges for treatment of a real patient's brain with three mono-energetic arcs according to aspects of the present invention.

On the bases that a proton gantry rotates with an angular speed of 1 revolution per minute, the amount of time required to complete each of the beam ON/OFF sequences (and therefore the treatment time) presented in FIGS. 12, 13, and 14 is 30 sec, 52.7 sec and 71.4 sec respectively. Thus, it is calculable that the Proton Modulated Arc Therapy ("PMAT") treatments are faster (minimum room time (MRT)=patient setup+30 sec+patient unload) or of similar duration (MRT=patient setup+75 sec+patient unload) than the SFO/MFO treatments, assuming that the patient load, setup, and unload time requirements are the same for each treatment plan, and considering that each beam in the SFO or MFO plans need be loaded and reset from inside the room as well as that sometimes a couch quick between beams is also needed.

Figure 10:
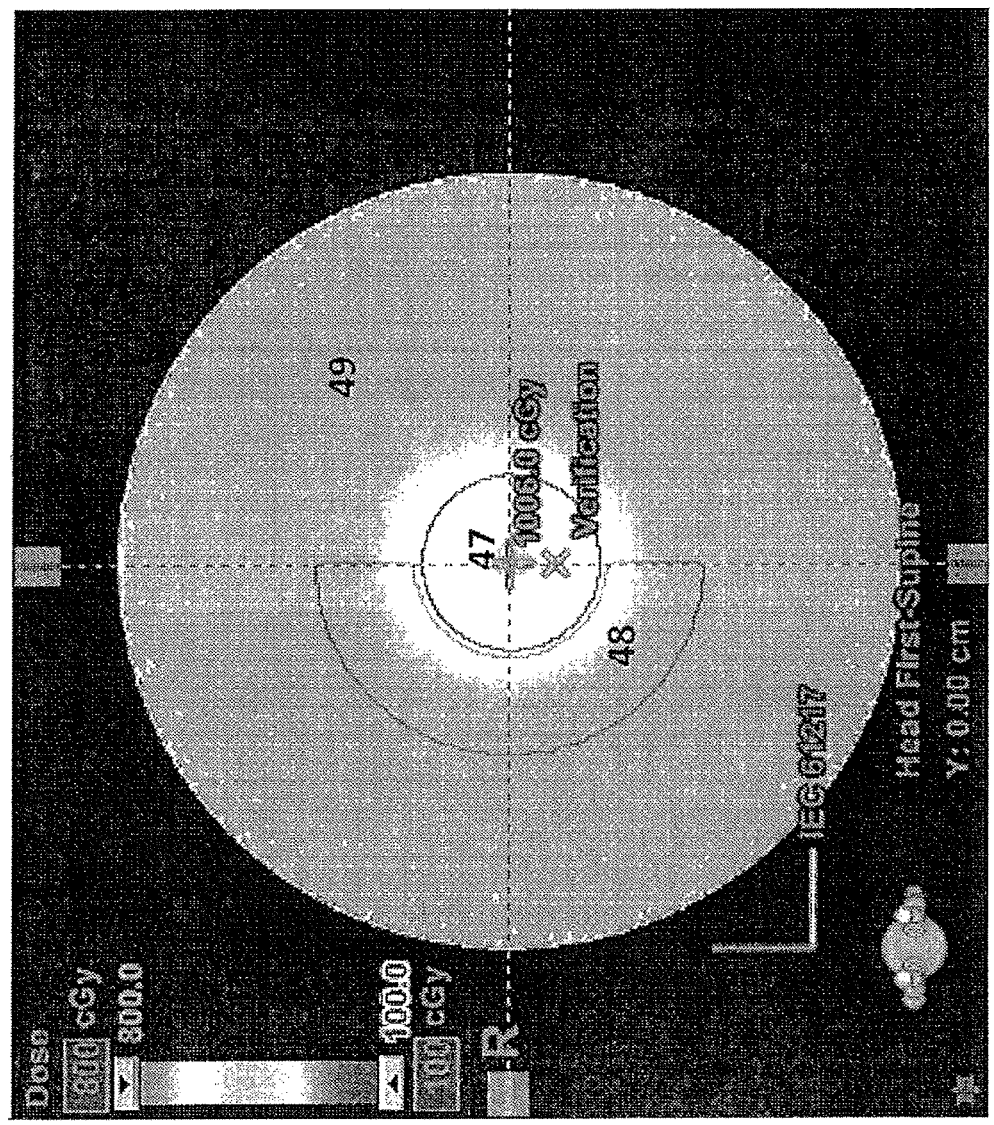
FIG. 10 is an image of the linear energy transfer (LET) distribution in a circular uniform phantom containing a defined symmetrical planning target volume that has been irradiated with charged particles according to aspects of the present invention.

Example 5—Linear Energy Transfer (LET) Distribution with Proton Modulated Arc Therapy LET is commonly used as an indicator of the biological power of the dose. The higher the LET, the higher the biological power of the dose. FIG. 10 shows the LET distribution associated with proton modulated arc therapy. Planning target volume 47 received an LET in excess of 8 keV/μm while OARs 48 and 49 received very low LET values.

Example 6a—Developing a PMAT Treatment Plan for a Uniform Elliptical Phantom

The objective was to treat the central cylindrical structure using the above prescription delivered with 37 fields separated every 5° over a 180° arc going from left to right of the phantom. The OAR was an annular structure.

The range and modulation required from each field of the arc to provide full dose coverage to the target were calculated (each field has its own range and spread out Bragg peak (SOBP) width). The water equivalence distance ("WED") was also determined. This calculation, which was done in single field optimization, provides the calculated ranges ($R_{TPS}$) appearing in table 2. These ranges correspond to the energy of the most distal layer of each beam. As the method described in this example is premised on all beams stopping inside the target, the final range for each beam was obtained from:

$$R_{PMAT} = R_{TPS} - \frac{MOD_{TPS}}{2}$$

Where $R_{PMAT}$ corresponds to the final range for each beam used for the PMAT calculation, and $MOD_{TPS}$ corresponds to the modulation obtained from the TPS for each beam during the raw (free range and modulation) calculation. Table 2 is provided below.

TABLE 2

Relevant beam data to make PMAT plans for the uniform phantom case

| Bm. No. | Bm. Angl. | Distal Range | SOBP width | $R_{PMAT}$ | WED | 1E | 2E | 3E |
|---|---|---|---|---|---|---|---|---|
| 1 | 90 | 17.38 | 4.24 | 15.26 | 15.22 | 12.65 | 13.95 | 14.39 |
| 2 | 85 | 17.35 | 4.48 | 15.11 | 15.15 |  |  |  |
| 3 | 80 | 17.16 | 4.56 | 14.88 | 14.88 |  |  |  |
| 4 | 75 | 16.90 | 4.80 | 14.50 | 14.56 |  |  |  |
| 5 | 70 | 16.58 | 4.93 | 14.12 | 14.19 |  |  |  |
| 6 | 65 | 16.25 | 5.21 | 13.65 | 13.74 |  |  |  |
| 7 | 60 | 15.78 | 5.26 | 13.15 | 13.24 |  |  | 12.65 |
| 8 | 55 | 15.38 | 5.34 | 12.71 | 12.75 |  |  |  |
| 9 | 50 | 14.82 | 5.21 | 12.22 | 12.24 |  | 11.34 |  |
| 10 | 45 | 14.35 | 5.13 | 11.79 | 11.84 |  |  |  |
| 11 | 40 | 13.95 | 5.07 | 11.42 | 11.39 |  |  | 10.91 |
| 12 | 35 | 13.56 | 4.96 | 11.08 | 11.15 |  |  |  |
| 13 | 30 | 13.21 | 4.80 | 10.81 | 10.8 |  |  |  |
| 14 | 25 | 12.90 | 4.70 | 10.55 | 10.53 |  |  |  |
| 15 | 20 | 12.65 | 4.54 | 10.38 | 10.35 |  |  |  |
| 16 | 15 | 12.43 | 4.41 | 10.23 | 10.23 |  |  |  |
| 17 | 10 | 12.31 | 4.29 | 10.17 | 10.07 |  |  |  |
| 18 | 5 | 12.18 | 4.20 | 10.08 | 10.08 |  |  |  |
| 19 | 0 | 12.11 | 4.15 | 10.04 | 10.03 |  |  |  |
| 20 | 355 | 12.17 | 4.17 | 10.09 | 10.06 |  |  |  |
| 21 | 350 | 12.25 | 4.32 | 10.09 | 10.06 |  |  |  |
| 22 | 345 | 12.38 | 4.38 | 10.19 | 10.22 |  |  |  |
| 23 | 340 | 12.60 | 4.49 | 10.36 | 10.33 |  |  |  |
| 24 | 335 | 12.83 | 4.68 | 10.49 | 10.5 |  |  |  |
| 25 | 330 | 13.10 | 4.74 | 10.73 | 10.76 |  |  |  |
| 26 | 325 | 13.41 | 4.84 | 10.99 | 11.05 |  |  |  |
| 27 | 320 | 13.80 | 4.96 | 11.32 | 11.33 |  |  |  |
| 28 | 315 | 14.19 | 5.09 | 11.65 | 11.73 |  |  |  |
| 29 | 310 | 14.59 | 5.10 | 12.04 | 12.09 |  |  | 12.65 |
| 30 | 305 | 15.09 | 5.27 | 12.46 | 12.57 |  |  |  |
| 31 | 300 | 15.55 | 5.27 | 12.92 | 13.06 |  | 13.95 |  |
| 32 | 295 | 15.94 | 5.16 | 13.36 | 13.55 |  |  |  |
| 33 | 290 | 16.35 | 5.01 | 13.85 | 13.96 |  |  | 14.39 |
| 34 | 285 | 16.63 | 4.73 | 14.27 | 14.32 |  |  |  |
| 35 | 280 | 16.90 | 4.63 | 14.59 | 14.63 |  |  |  |
| 36 | 275 | 17.00 | 4.39 | 14.81 | 14.89 |  |  |  |
| 37 | 270 | 17.07 | 4.20 | 14.97 | 14.95 |  |  |  |

Table 2 provides the collection of ranges to use if one (1E) or two (2E) or three (3E) mono-energetic arcs were used. As set forth above, the inventor identified a potential range or combination of ranges that requires the shortest arc trajectory with the highest possible dose conformity to the target. The ranges to use in the 1E, 2E or 3E arcs were based on a graphical method explained below.

Figure 15:
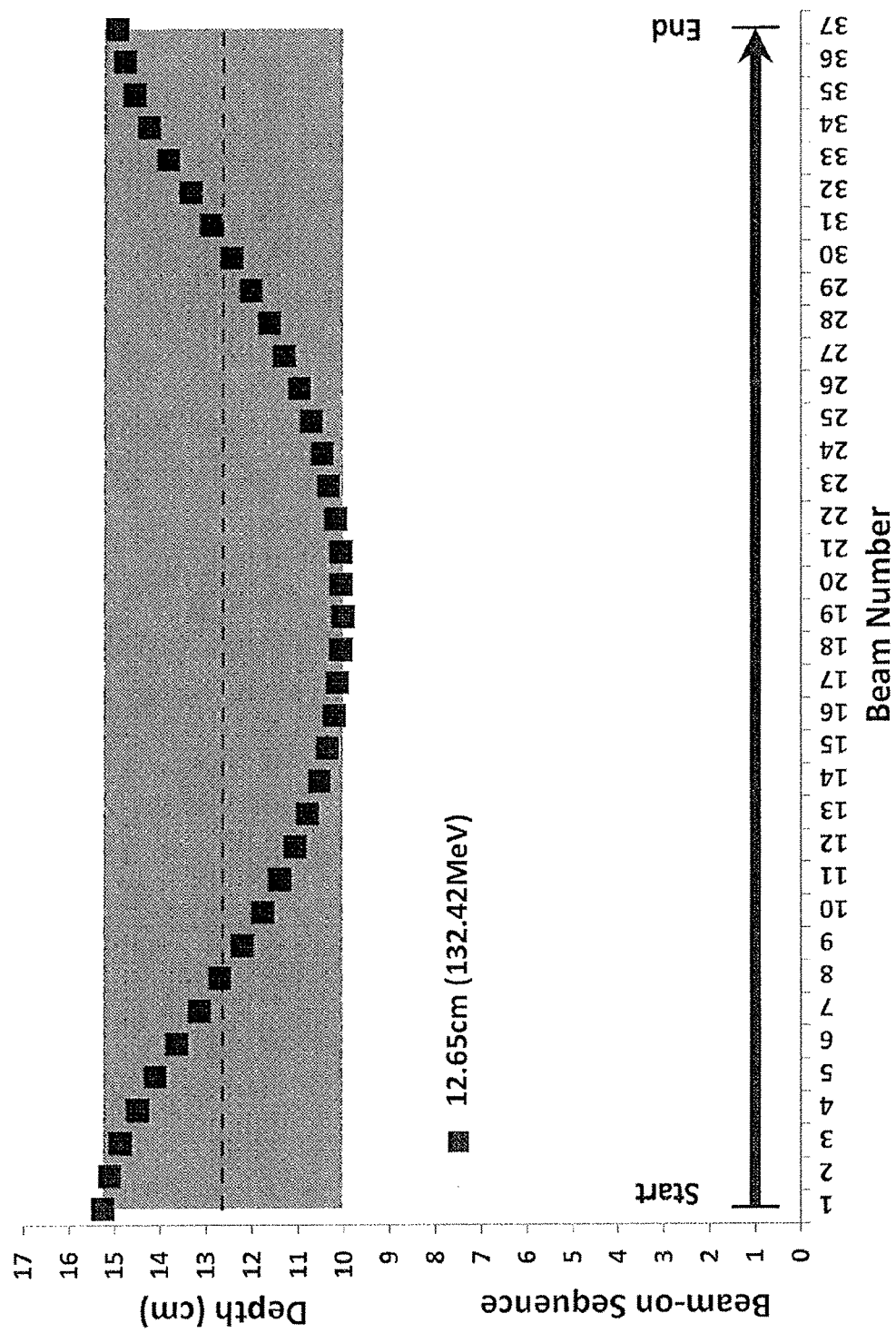
FIG. 15 is a schematic of the beam range for treatment of a uniform elliptical phantom with one mono-energetic arc according to aspects of the present invention.
Figure 16:
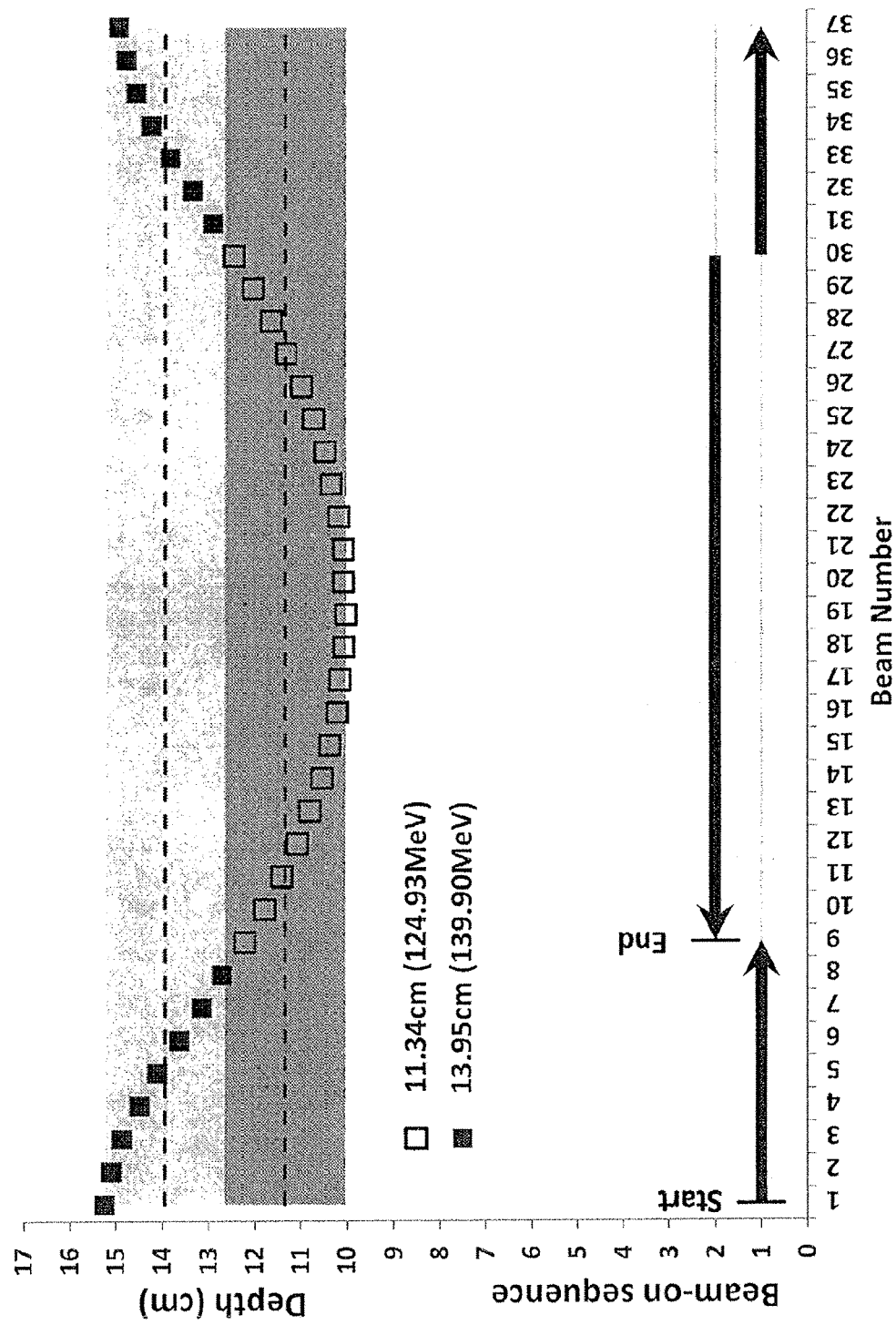
FIG. 16 is a schematic of the beam ranges for treatment of a uniform elliptical phantom with two mono-energetic arcs according to aspects of the present invention.
Figure 17:
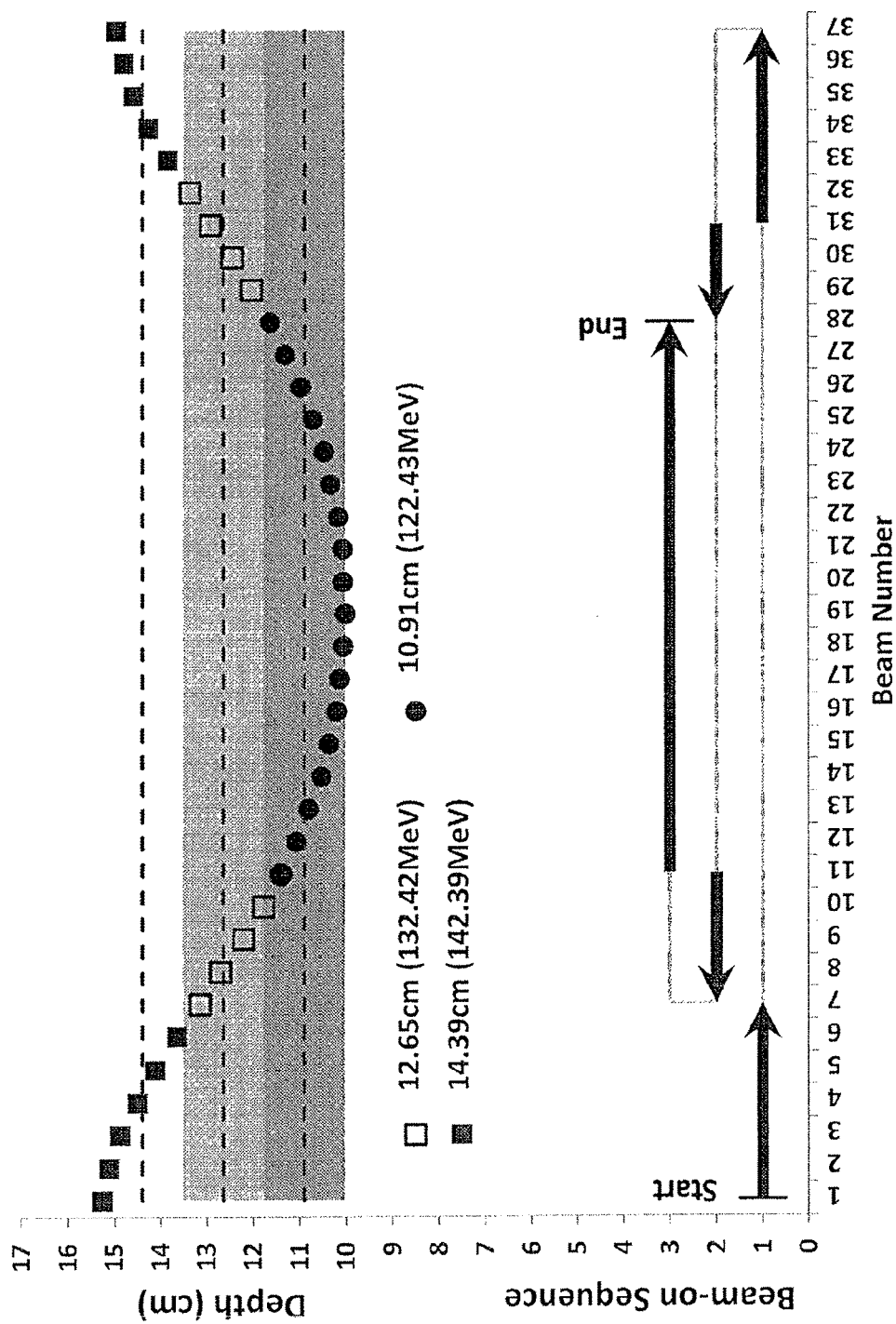
FIG. 17 is a schematic of the beam ranges for treatment of a uniform elliptical phantom with three mono-energetic arcs according to aspects of the present invention.

To find the single energy solution, presented in FIG. 15, the middle range between the maximum and the minimum of the ranges presented in table 2 was used. To calculate the 2 ranges required for FIG. 16, the range difference between maximum and minimum was equally divided in two regions, and the mid-point of the beam ranges included in each of these two regions provided the solution ranges for each mono-energetic arc: 11.34 cm and 13.95 cm. As illustrated in FIGS. 15, 16, and 17, as the number of mono-energetic arcs used increases, the distance of the points to the dashed line decreases.

The lines and arrows in the lower part of FIGS. 15, 16, and 17 represent the beam ON and OFF sequence that could be used to deliver the mono-energetic arcs in each of the phantom cases. The sequence was based on identifying the shortest total gantry rotation to deliver all required arcs, which would represent the shortest treatment delivery time.

Example 6b—Developing a PMAT Treatment Plan for a Non-Uniform Elliptical Phantom The objective was to treat a half annular target structure wrapped around a cylindrical OAR. PMAT treatment included an arc with 37 fields every 5 degrees over a 180 degree tilted arc, whereby beam angles 1-3 passed through less inhomogeneity than beam angles 24-27. The first angle of the arc was set at 65 degrees from the vertical.

Aspects of the process used in Example 6a were employed to determine the range required to produce PMAT plans, whereby the distal edge of the SOBP was obtained from the most distal point of the distal edge and the proximal edge of the SOBP was determined from the most proximal point of the proximal edge of the target structure.

Figure 18:
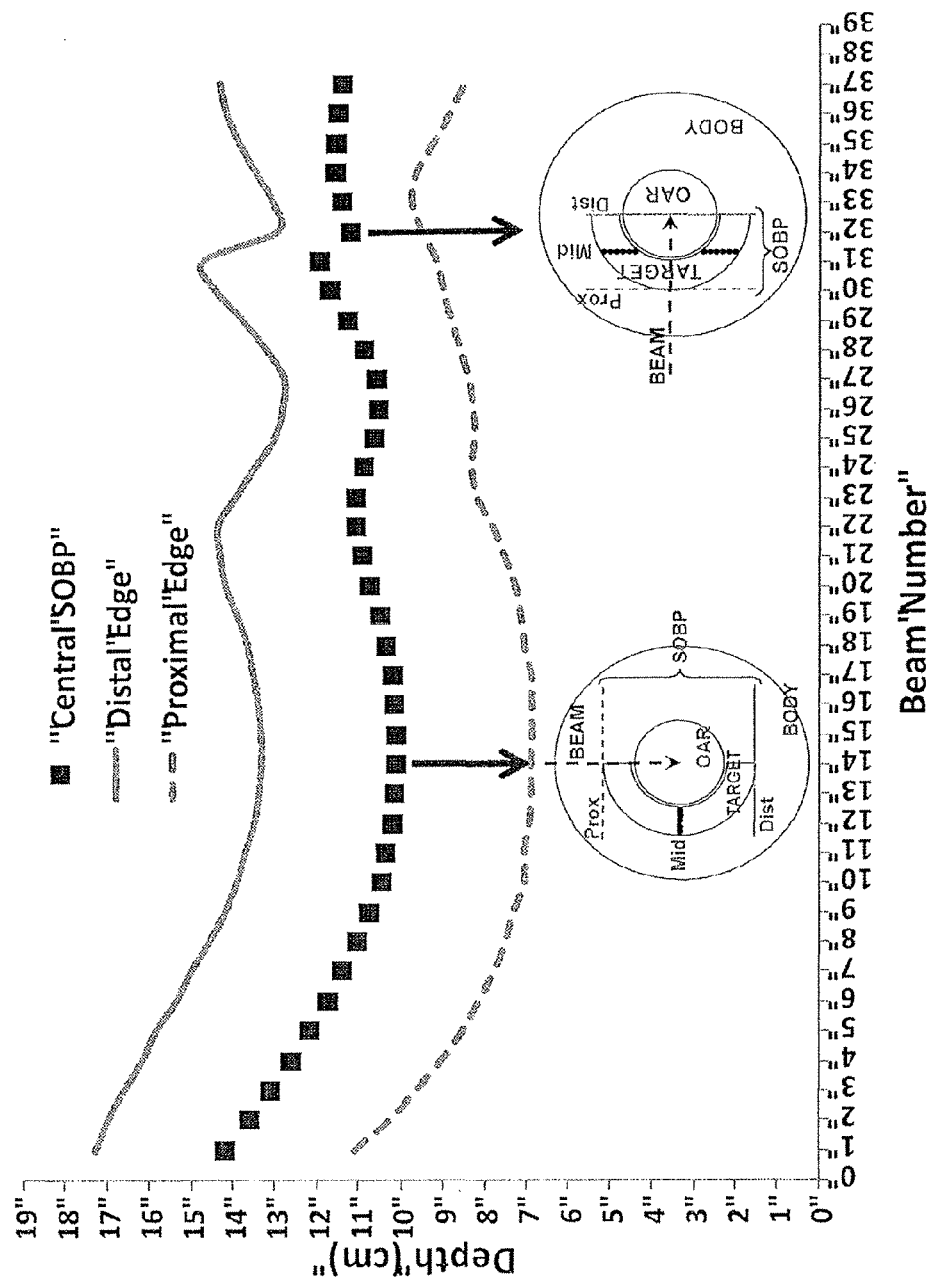
FIG. 18 is a schematic depicting an irradiation process in accordance with aspects of the present invention.
Figure 19:
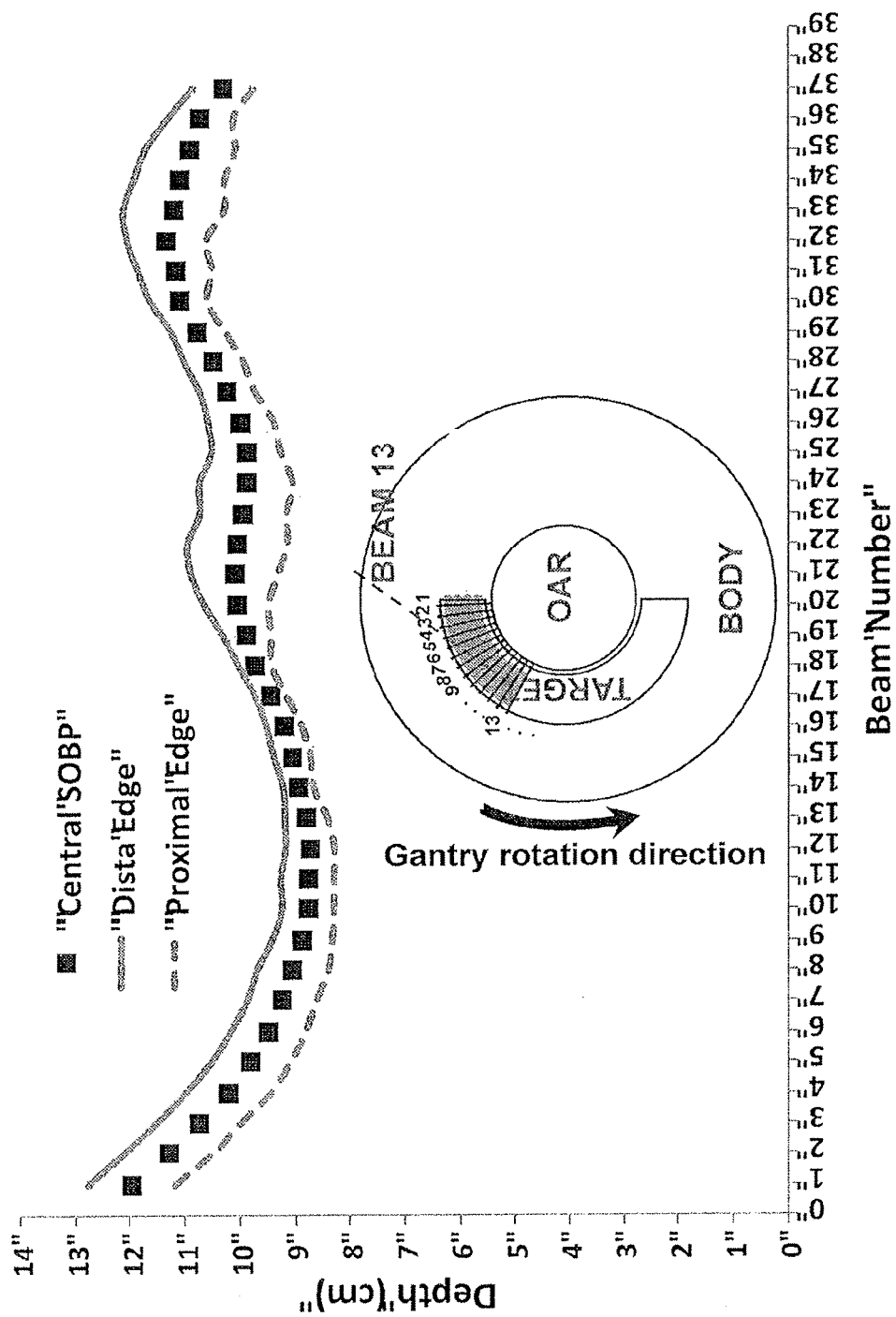
FIG. 19 is a schematic depicting an irradiation process for non-uniform elliptical phantom according to aspects of the present invention.
Figure 20:
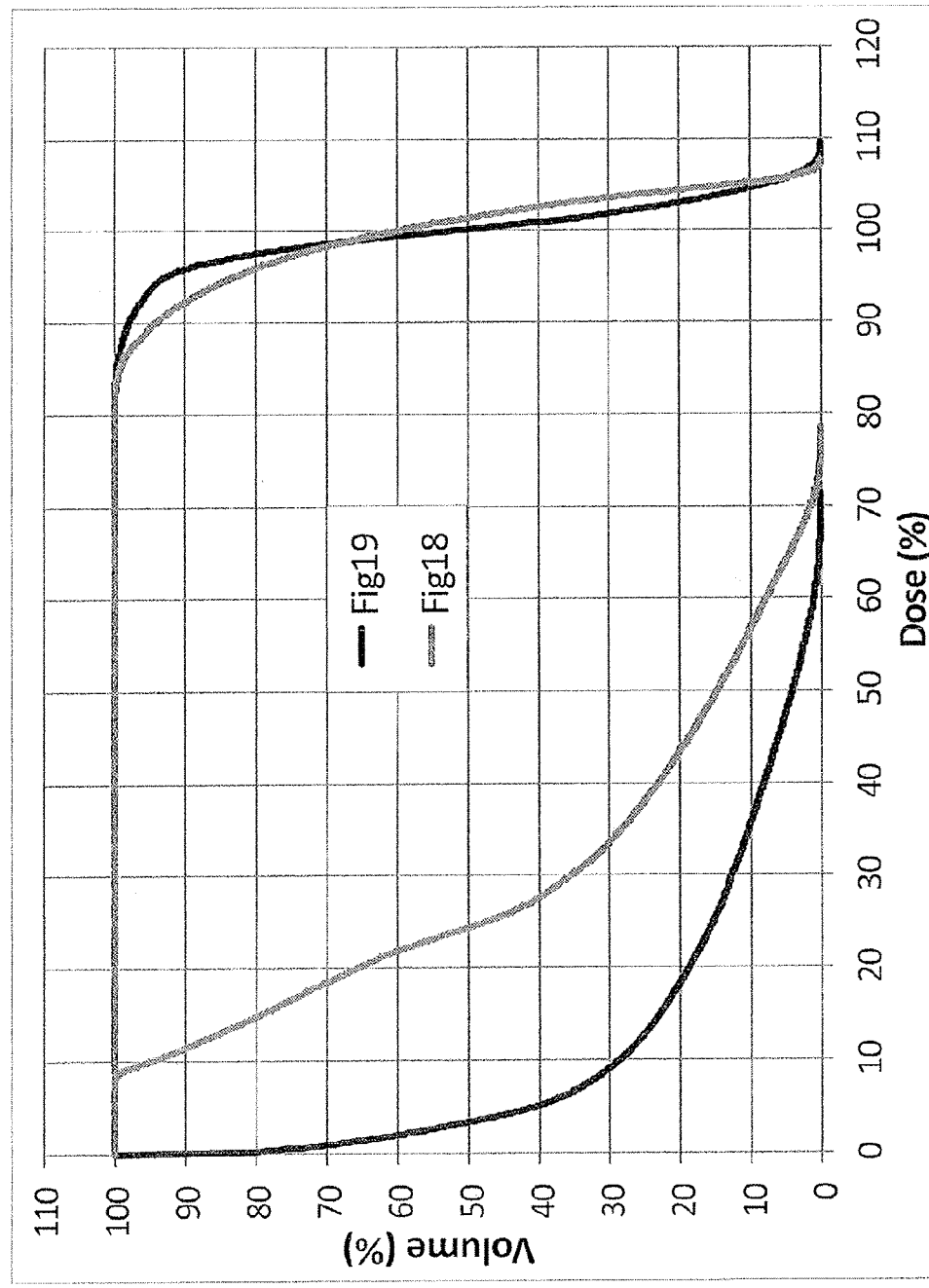
FIG. 20 is an image of the dose distribution when a single mono-energetic arc is planned according to the data presented in FIGS. 18 and 19.

A contouring technique, different from the technique of Example 6a, was employed to enable optimization of the uniformity of the arc by way of modifying the SOBP width. The contouring technique employed included subdividing the target structure into multiple sub-targets that served as target structures for each beam. Splitting the target into multiple sub-targets may reduce the heterogeneity of the SOBP width variation across the arc and enable the dosage to be delivered by alternative directions. The sub-targets were produced by splitting the target in wedges every 5 degrees, thereby creating 37 sub-targets, one for each beam (e.g., sub-target 1 served as the target for beam 1, sub-target 2 served as target for beam 2, etc.). FIG. 18 illustrates the difference between the mid-SOBP range and the target WED for each beam angle. FIG. 19 depicts the technique used to irradiate the target in the case of the non-uniform elliptical phantom. FIG. 20 illustrates the difference in the dose distribution when a single mon-energetic arc is planned using the raw data presented in FIGS. 18 and 19. The inventors found that the method employed in this Example may provide more conformal and homogenous dose distribution than the method in Example 6a.

Figure 21:
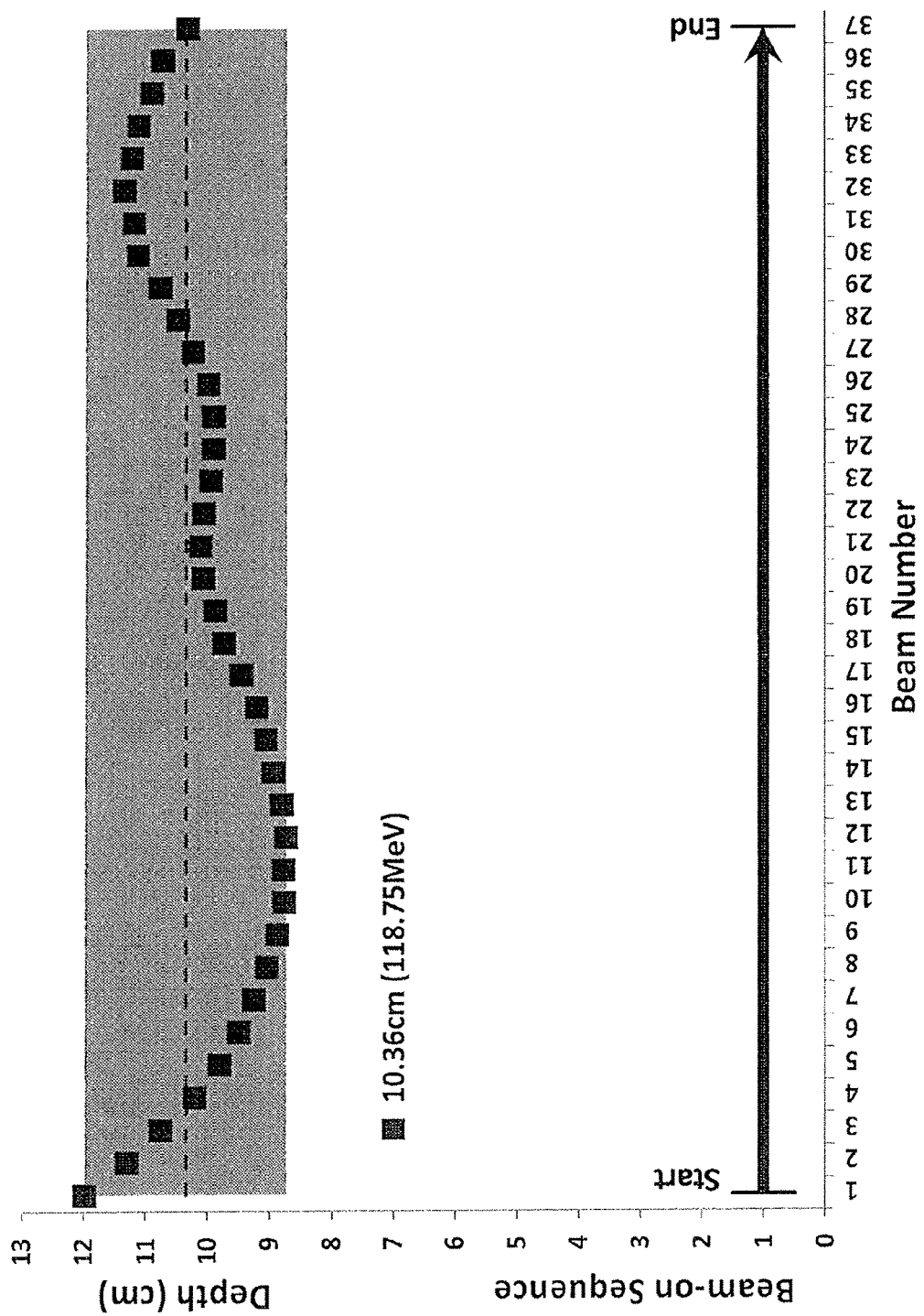
FIG. 21 is a schematic of the range selection process for a non-uniform elliptical phantom using one mono-energetic arc in accordance with aspects of the present invention.
Figure 22:
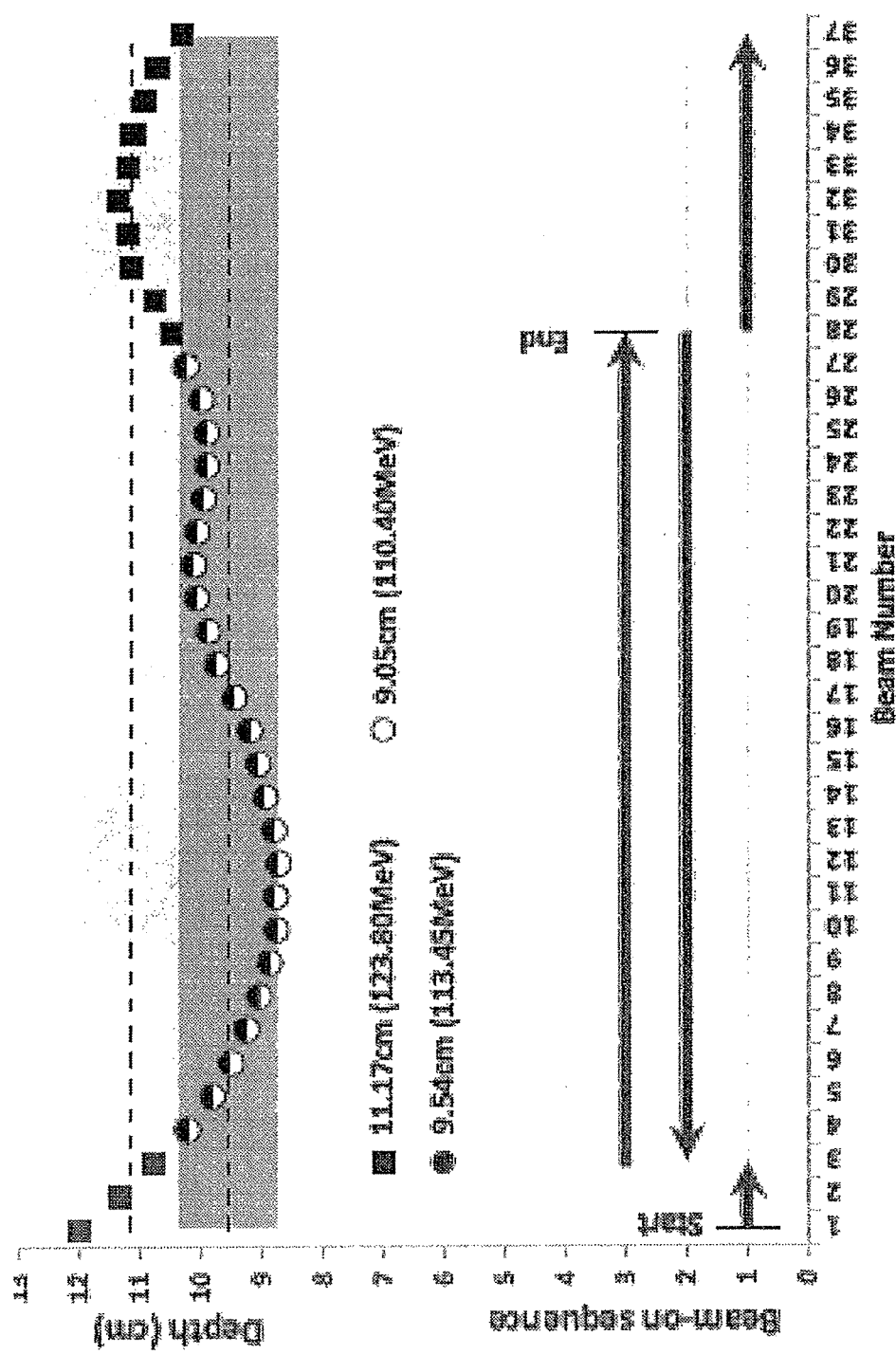
FIG. 22 is a schematic of the range selection process for a non-uniform elliptical phantom using two mono-energetic arcs according to aspects of the present invention.
Figure 23:
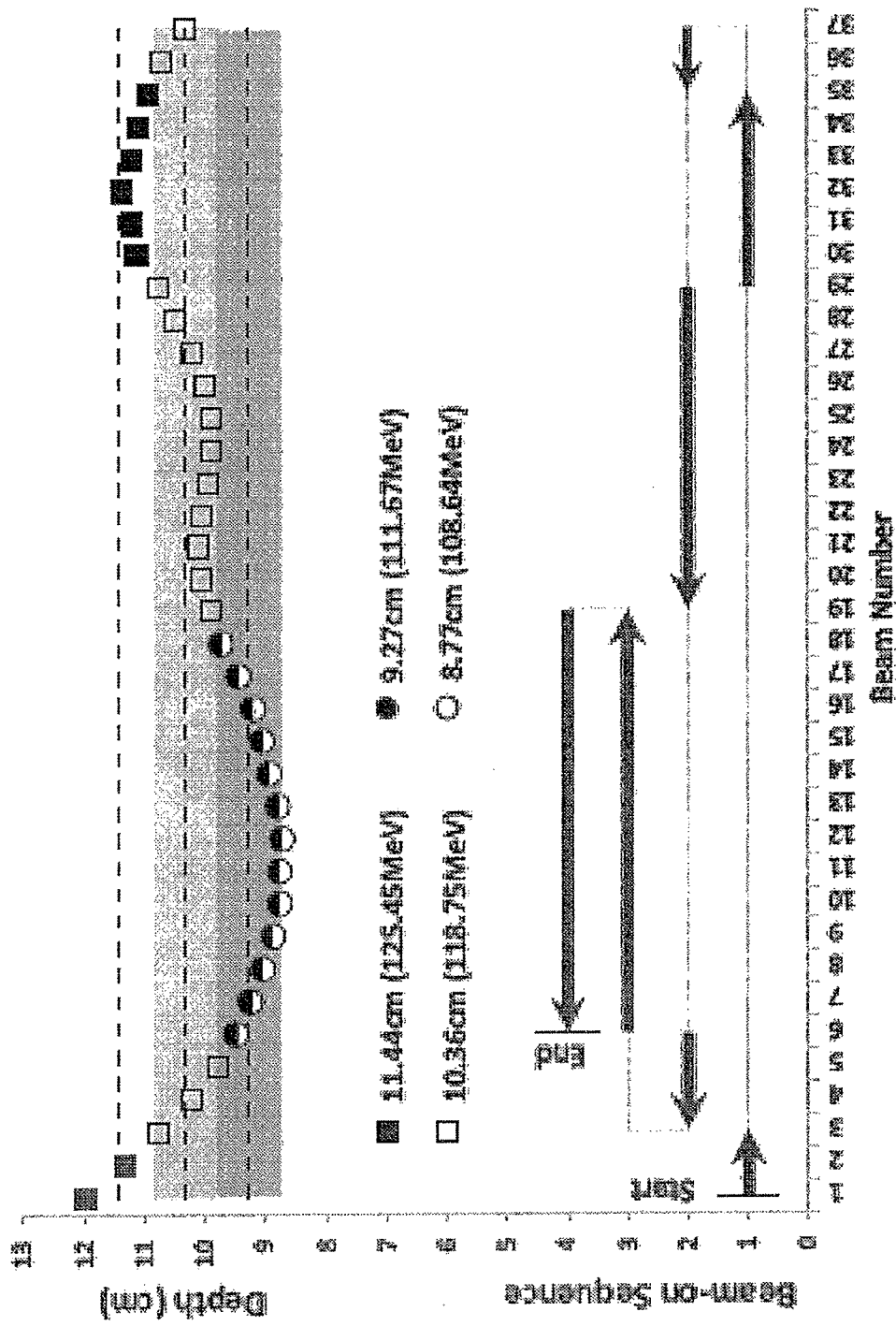
FIG. 23 is a schematic of the range selection process for a non-uniform elliptical phantom using three mono-energetic arcs in accordance with aspects of the present invention.

The range selection for each mono-energetic arc solution was determined according to the methodologies explained above, e.g., Example 6a. FIGS. 21-23 depict the range selection process for each beam as the number of arcs is increased from 1 to 3. The calculations employed to provide Table 3, shown below, used a lateral spot spacing of 0.5 cm.

TABLE 3

Relevant beam data used to plan PMAT in non-uniform phantom case

| Beam Number | Beam Angle | Distal Range | SOBP Width | $R_{PMAT}$ | WED | 1E | 2E | 3E |
|---|---|---|---|---|---|---|---|---|
| 1 | 65 | 12.77 | 1.57 | 11.99 | 12.67 | 10.36 | 11.17 | 11.44 |
| 2 | 60 | 12.12 | 1.63 | 11.31 | 12.98 | | | |
| 3 | 55 | 11.52 | 1.53 | 10.76 | 13.15 | | | 10.36 |
| 4 | 50 | 10.98 | 1.55 | 10.21 | 12.53 | 9.54 | 9.05 | |
| 5 | 45 | 10.52 | 1.44 | 9.80 | 12.10 | | | |
| 6 | 40 | 10.17 | 1.36 | 9.49 | 11.69 | | 9.27 | 8.77 |
| 7 | 35 | 9.88 | 1.26 | 9.25 | 11.22 | | | |
| 8 | 30 | 9.69 | 1.29 | 9.05 | 10.92 | | | |
| 9 | 25 | 9.42 | 1.09 | 8.88 | 10.66 | | | |
| 10 | 20 | 9.24 | 0.95 | 8.77 | 10.40 | | | |
| 11 | 15 | 9.26 | 0.97 | 8.78 | 10.19 | | | |
| 12 | 10 | 9.18 | 0.90 | 8.73 | 10.09 | | | |
| 13 | 5 | 9.19 | 0.77 | 8.81 | 10.06 | | | |
| 14 | 0 | 9.22 | 0.55 | 8.95 | 9.98 | | | |
| 15 | 355 | 9.39 | 0.66 | 9.06 | 10.05 | | | |
| 16 | 350 | 9.53 | 0.65 | 9.21 | 10.07 | | | |
| 17 | 345 | 9.74 | 0.58 | 9.45 | 10.26 | | | |
| 18 | 340 | 10.04 | 0.61 | 9.74 | 10.30 | | | |
| 19 | 335 | 10.32 | 0.88 | 9.88 | 10.57 | | | 10.36 |
| 20 | 330 | 10.66 | 1.17 | 10.08 | 10.85 | | | |
| 21 | 325 | 10.90 | 1.58 | 10.11 | 11.12 | | | |
| 22 | 320 | 10.97 | 1.82 | 10.06 | 11.52 | | | |
| 23 | 315 | 10.74 | 1.58 | 9.95 | 11.90 | | | |
| 24 | 310 | 10.75 | 1.70 | 9.90 | 12.39 | | | |
| 25 | 305 | 10.53 | 1.26 | 9.90 | 12.93 | | | |
| 26 | 300 | 10.59 | 1.20 | 9.99 | 12.45 | | | |
| 27 | 295 | 10.75 | 1.02 | 10.24 | 12.13 | | | |
| 28 | 290 | 11.03 | 1.08 | 10.49 | 11.90 | | 11.17 | |
| 29 | 285 | 11.27 | 1.00 | 10.77 | 12.02 | | | |
| 30 | 280 | 11.65 | 1.04 | 11.13 | 12.31 | | | 11.44 |
| 31 | 275 | 11.88 | 1.36 | 11.20 | 12.61 | | | |
| 32 | 270 | 12.08 | 1.45 | 11.36 | 12.91 | | | |
| 33 | 265 | 12.15 | 1.85 | 11.23 | 13.61 | | | |
| 34 | 260 | 11.95 | 1.66 | 11.12 | 13.91 | | | |
| 35 | 255 | 11.74 | 1.65 | 10.92 | 13.17 | | | |

TABLE 3-continued

Relevant beam data used to plan PMAT in non-uniform phantom case

| Beam Number | Beam Angle | Distal Range | SOBP Width | $R_{PMAT}$ | WED | 1E | 2E | 3E |
|---|---|---|---|---|---|---|---|---|
| 36 | 250 | 11.34 | 1.21 | 10.74 | 13.00 | | | 10.36 |
| 37 | 245 | 10.87 | 1.09 | 10.33 | 12.69 | | | |

Additionally or alternatively, the use of PMAT algorithms, which account for the dose in between beams not accounted for in the present step-and-shoot mode used in this Example, may desirably improve the efficacy of the treatment. For example, as can be seen in the 2E and 3E cases, the two layers the TPS imposes, even with the SOBP width at 0 cm, are very close to one another; e.g., 2E beams 4 to 27 include 9.54 cm at 113.45 MeV and 9.05 cm at 110.40 MeV and 3E beams 6 to 18 include 9.27 cm at 111.66 MeV and 8.77 cm at 108.64 MeV. Without intending to be limited to any particular theory, it is believed that this effect results from current TPS providing homogenous dose coverage to the target structure at any given angle.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A method for irradiating a planning target volume with charged particles, comprising the steps of:
    delivering the charged particles to the planning target volume with a charged particle therapy system including:
        a charged particle beam path; and
        one or more charged particle beam path direction devices from the group consisting of a gantry configured to rotate about the planning target volume and a patient positioning device configured to rotate the planning target volume;
    rotating the charged particle beam path direction devices, during an irradiation session, to a plurality of positions within at least one arc about the planning target volume; and
    during the rotation, irradiating the planning target volume with the charged particles at a first energy level at one or more of the plurality of positions such that, at each of the one or more of the plurality of positions, the charged particle beam path terminates within the planning target volume to produce a Bragg peak within the planning target volume.

2. The method of claim 1, wherein the plurality of positions are located at various points within an arc about the planning target volume.

3. The method of claim 1, where the plurality of positions are within the same plane of rotation.

4. The method of claim 1, wherein the plurality of positions are within multiple planes of rotations.

5. The method of claim 1, further comprising rotating the gantry a plurality of arcs about the planning treatment volume, wherein each arc has the same center of rotation.

6. The method of claim 1, further comprising rotating the gantry a plurality of arcs about the planning treatment volume, wherein each arc has a different center of rotation.

7. The method of claim 1, wherein the rotating step comprises continuously rotating the gantry and only irradiating the planning target volume at the plurality of positions.

8. The method of claim 7, wherein the rotating step comprises shutting off the charged particle beam path at positions other than the plurality of positions.

9. The method of claim 1, wherein the rotating step comprises rotating the gantry at least twice about the planning target volume and wherein the irradiating step comprises, during the first rotation, delivering charged particles at a first energy level to the planning target volume at a first set of positions within the plurality of positions and, during the second rotation, delivering charged particles at a second energy level at a second set of positions within the plurality of positions.

10. The method of claim 9, wherein the first set of positions are different from the second set of positions.

11. The method of claim 1, wherein the rotating step comprises rotating the gantry at least three times about the planning target volume and wherein the irradiating step comprises, during the first rotation, delivering charged particles at a first energy level to the planning target volume at a first set of positions within the plurality of positions and, during the second rotation, delivering charged particles at a second energy level to the planning target volume at a second set of positions within the plurality of positions and, during the third rotation, delivering charged particles at a third energy level at a third set of positions within the plurality of positions.

12. The method of claim 1, wherein the charged particle therapy system comprises a pencil beam scanning system.

13. The method of claim 9, further comprising, prior to the delivering step, the step of subdividing the planning target volume into a plurality of sub-targets that form the plurality of positions.

14. A charged particle system comprising
    a charged particle beam path including charged particles; and
    one or more charged particle beam path direction devices from the group consisting of a gantry configured to rotate about a planning target volume and a patient positioning device configured to rotate the planning target volume, the charged particle beam path direction devices configured to deliver charged particles while rotating, such that the charged particle beam path terminates within the planning target volume to produce a Bragg peak within the planning target volume.

15. The system of claim 14, further configured to deliver the charged particle beam in pencil beam scanning mode.

16. The charged particle system of claim 14, wherein the gantry is configured to rotate a plurality of times about a planning target volume and to deliver charged particles at a distinct energy level during each rotation.

17. A method for irradiating a planning target volume with charged particles, comprising the steps of:

delivering the charged particles to the planning target volume with a charged particle therapy system including:
- a charged particle beam path; and
- one or more charged particle beam path direction devices from the group consisting of a gantry configured to rotate about the planning target volume and a patient positioning device configured to rotate the planning target volume;

rotating the charged particle beam path with reference to the planning target volume, during an irradiation session, to a plurality of positions within at least one arc about the planning target volume; and during the rotation, irradiating the planning target volume with the charged particles at a first energy level at one or more of the plurality of positions.

18. The method of claim 17, wherein at each of the one or more of the plurality of positions, the charged particle beam path terminates in a central region of the planning target volume to produce a Bragg peak in the central region.

19. The method of claim 1, wherein the charged particle beam path terminates within a central region of the planning target volume.

20. The method of claim 1, wherein the charged particle beam path terminates within the planning target volume to produce a Bragg peak within the central region of the planning target volume.

21. The charged particle system of claim 14, wherein the charged particle beam path terminates within a central region of the planning target volume to produce a Bragg peak within the central region.

* * * * *